(12) United States Patent
Skelton et al.

(10) Patent No.: US 8,231,556 B2
(45) Date of Patent: Jul. 31, 2012

(54) OBTAINING BASELINE PATIENT INFORMATION

(75) Inventors: Dennis M. Skelton, Bloomington, MN (US); Jon P. Davis, St. Michael, MN (US); Dennis Bourget, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 541 days.

(21) Appl. No.: 12/433,749

(22) Filed: Apr. 30, 2009

(65) Prior Publication Data

US 2010/0010387 A1 Jan. 14, 2010

Related U.S. Application Data

(60) Provisional application No. 61/080,000, filed on Jul. 11, 2008.

(51) Int. Cl.
*A61B 5/00* (2006.01)
*A61B 5/103* (2006.01)
*A61B 5/117* (2006.01)
*A61N 1/00* (2006.01)

(52) U.S. Cl. ............ 600/595; 600/300; 607/17; 607/18; 607/19; 607/30; 607/46; 607/48; 607/62; 607/69; 607/70; 607/76

(58) Field of Classification Search .................. 600/300, 600/595; 607/17, 18, 19, 30, 46, 48, 62, 607/69, 70, 76
See application file for complete search history.

(56) References Cited

U.S. PATENT DOCUMENTS

| | | |
|---|---|---|
| 4,297,685 A | 10/1981 | Brainard, II |
| 4,365,633 A | 12/1982 | Loughman |
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |

(Continued)

FOREIGN PATENT DOCUMENTS

DE 19831109 1/2000

(Continued)

OTHER PUBLICATIONS

International Preliminary Report on Patentability Chapter I (IB/373), Jan. 11, 2011.*

(Continued)

*Primary Examiner* — Sean Dougherty
(74) *Attorney, Agent, or Firm* — Shumaker & Sieffert, P.A.

(57) ABSTRACT

The disclosure relates to a method and system for obtaining baseline patient information. In some examples, a method may include acquiring first patient data, wherein the first patient data comprises at least one of first posture state data indicative of a plurality of posture states of a patient during a first time period or first therapy adjustment data indicative of a plurality of patient therapy adjustments made during the first time period; generating baseline patient information based at least in part on the first patient data; and comparing the baseline patient information to patient information generated based on second patient data. Therapy is not delivered to the patient according to a detected posture state of the patient during the first time period, and therapy is delivered to the patient according to the detected posture state of the patient during the second time period.

31 Claims, 20 Drawing Sheets

U.S. PATENT DOCUMENTS

| | | |
|---|---|---|
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,070,568 B1 | 7/2006 | Koh |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al. |
| 7,214,197 B2 | 5/2007 | Prass |

| | | |
|---|---|---|
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,643,655 B2 | 1/2010 | Liang et al. |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 8,032,224 B2 * | 10/2011 | Miesel et al. ............ 607/46 |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0097814 A1 | 5/2004 | Navakatikyan et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0107722 A1 | 5/2005 | Ozaki et al. |
| 2005/0113710 A1 | 5/2005 | Stahmann et al. |
| 2005/0113887 A1 | 5/2005 | Bauhahn et al. |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118054 A1 | 5/2007 | Pinhas et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |

| | | |
|---|---|---|
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0275349 A1 | 11/2008 | Halperin et al. |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| DE | 10024103 | 11/2001 |
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

Written Opinion of the International Search Authority, Jan. 11, 2011.*

International Search Report, Jan. 14, 2011.*

"Analysis of heart rate dynamics by methods derived from non-linear mathematics: Clinical applicability and prognostic significance," http://herkules.oulu.fi.isbn9514250133/html, 4 pp., 2004.

"Design Competition: Runners-Up for the Best Three Designs," EPN, vol. 26, No. 1, 1 pg., 2002.

IBM and Citizen Watch develop Linux-Based "WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308,1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.

Husak, "Model of Tilt Sensor Systems," ICECS 2002, $9^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/edp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp. 2008.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from the Accelerometer Data for Videogame Applications," http://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp., Mar. 2007.

Tuisku, "Motor Activity Measured by Actometry in Neuropsychiatric Disorders," Department of Psychiatry, University of Helsinki, Helsinki, Finland, 115 pp., 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.

PCT/US09/49241: International Search Report and Written Opinion dated Oct. 7, 2009, 14 pp.

U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

OBTAINING BASELINE PATIENT INFORMATION

This application claims the benefit of U.S. Provisional Application No. 61/080,000, filed Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure describes medical devices, systems and techniques related to the delivery of therapy to a patient by a medical device. The therapy may include electrical stimulation therapy or other therapies. A medical device may be configured to monitor posture state of patient and/or patient therapy adjustments and, in some examples, deliver therapy to a patient according to the detected posture state of the patient. The delivery of therapy to a patient by a medical device according to the detected patient posture state may generally be referred to as posture-responsive therapy, and may include detecting the posture state of a patient, e.g., via one or more posture sensors, and adjusting the value of one or more therapy parameters based on the detected patient posture state.

A medical device may monitor the posture state of a patient over a period of time during which posture-responsive therapy is not delivered to a patient. For example, during such a time period, a medical device may deliver therapy to a patient albeit on a non-posture responsive basis, i.e., the therapy is not delivered according to the detected patient posture state. Alternatively, a patient may not receive therapy in general during the time period in which the patient posture state is monitored by the medical device. The period of time may include a period of time prior to that of period when a patient receives posture-responsive therapy, a period of time after the termination of posture-responsive therapy, or any combination thereof. Additionally or alternatively, a medical device may monitor the number of therapy adjustments made by a patient over a period of time during which posture-responsive therapy is not delivered to a patient. For example, during such a time period, a medical device may deliver therapy to a patient albeit on a non-posture responsive basis, i.e., the therapy is not delivered according to the detected patient posture state.

By monitoring the patient posture state and/or patient therapy adjustments, the medical device may gather patient data that includes one or more of posture state data indicative of the patient posture state during the time period when the patient was not receiving posture-responsive therapy and therapy adjustment information indicative of patient therapy adjustments made during the time period when the patient was not receiving posture-responsive therapy. Using the patient data gathered during that time period, baseline patient information may then be generated. In some examples, the baseline patient information may include baseline posture state information, such as, e.g., baseline proportional posture information, baseline sleep quality information, or baseline posture state transition information. Alternatively or additionally, the baseline patient information may include baseline therapy adjustment information, such as, e.g., the number of therapy adjustments made by patient over all or a portion of the time period.

The generated baseline patient information may then be compared to patient information that has been generated based on patient data gathered over a time period during which the patient received posture-responsive therapy from a medical device. In this manner, the baseline patient information may used as a reference point to evaluate one or more aspects of the posture-responsive therapy. For example, a medical device may present such information to a user, such as, a patient or clinician, so the user may evaluate the efficacy of one or more aspects of therapy in terms of the difference between patient posture state behavior and/or patient therapy adjustments before delivery of posture-responsive therapy versus a patient posture state behavior and/or patient therapy adjustments during a time period in which posture-responsive therapy is delivered to the patient. In view of the comparison of the baseline patient information to the patient information corresponding to a posture-responsive time period, the user may make an adjustment to one or more aspects of the posture-responsive therapy. In other examples, a medical device may automatically or semi-automatically adjust to one or more aspects of the posture-responsive therapy based on the comparison of the baseline patient information to the patient information corresponding to a posture-responsive time period.

In one example, the disclosure provides a method comprising acquiring first patient data, wherein the first patient data comprises at least one of first posture state data indicative of a plurality of posture states of a patient during a first time period or first therapy adjustment data indicative of a plurality of patient therapy adjustments made during the first time period; generating baseline patient information based at least in part on the first patient data; and comparing the baseline patient information to patient information generated based on second patient data, wherein the second patient data comprises at least one of second posture state data indicative of a plurality of posture states of a patient during a second time period or second therapy adjustment data indicative of a plurality of patient therapy adjustments over the second time period, wherein therapy is not delivered to the patient according to a detected posture state of the patient during the first time period, and therapy is delivered to the patient according to the detected posture state of the patient during the second time period.

In another example, the disclosure provides a system comprising a processor configured to acquire first patient data, generate baseline patient information based at least in part on the first patient data, and compare the baseline patient information to patient information generated based on second patient data, wherein the first patient data comprises at least one of first posture state data indicative of a plurality of posture states of a patient during a first time period or first therapy adjustment data indicative of a plurality of patient therapy adjustments made during the first time period, wherein the second patient data comprises at least one of second posture state data indicative of a plurality of posture states of a patient during a second time period or second therapy adjustment data indicative of a plurality of patient therapy adjustments over the second time period, wherein therapy is not delivered to the patient according to a detected posture state of the patient during the first time period, and therapy is delivered to the patient according to the detected posture state of the patient during the second time period.

In another example, the disclosure provides a computer readable storage medium having instructions that cause one or more processor to acquire first patient data, wherein the first patient data comprises at least one of first posture state data indicative of a plurality of posture states of a patient during a first time period or first therapy adjustment data indicative of a plurality of patient therapy adjustments made during the first time period; generate baseline patient information based at least in part on the first patient data; and compare the baseline patient information to patient information generated based on second patient data, wherein the second patient data comprises at least one of second posture state data indicative of a plurality of posture states of a patient during a second time period or second therapy adjustment data indicative of a plurality of patient therapy adjustments over the second time period, wherein therapy is not delivered to the patient according to a detected posture state of the patient during the first time period, and therapy is delivered to the patient according to the detected posture state of the patient during the second time period.

In another example, the disclosure provides a system comprising means for acquiring first patient data, wherein the first patient data comprises at least one of first posture state data indicative of a plurality of posture states of a patient during a first time period or first therapy adjustment data indicative of a plurality of patient therapy adjustments made during the first time period; means for generating baseline patient information based at least in part on the first patient data; and means for comparing the baseline patient information to patient information generated based on second patient data, wherein the second patient data comprises at least one of second posture state data indicative of a plurality of posture states of a patient during a second time period or second therapy adjustment data indicative of a plurality of patient therapy adjustments over the second time period, wherein therapy is not delivered to the patient according to a detected posture state of the patient during the first time period, and therapy is delivered to the patient according to the detected posture state of the patient during the second time period.

The details of one or more aspects of the disclosure are set forth in the accompanying drawings and the description below. Other features, objects, and advantages will be apparent from the description and drawings, and from the claims.

DETAILED DESCRIPTION

Figure 1A:
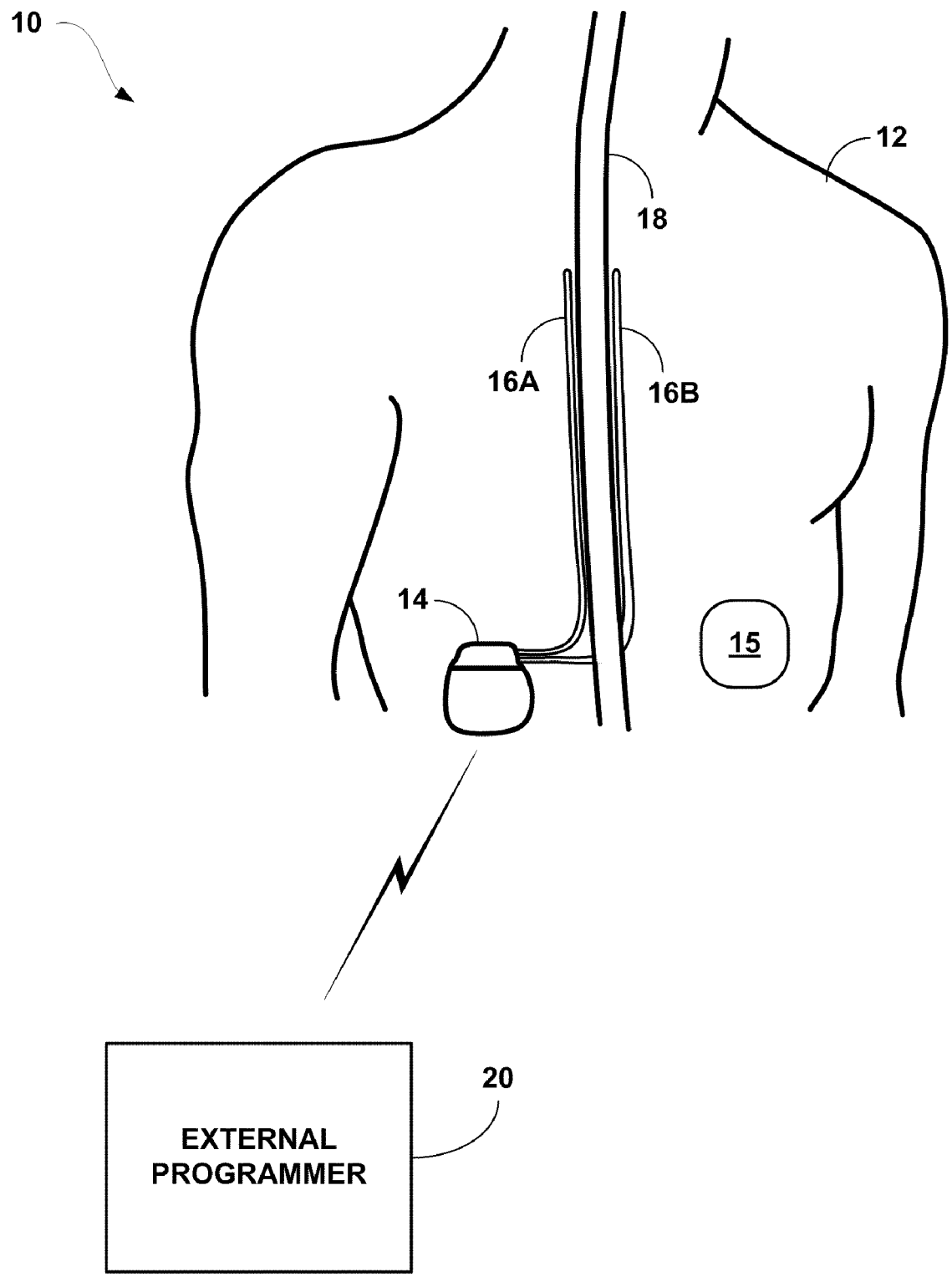
FIG. 1A is a conceptual diagram illustrating an example implantable stimulation system including two implantable stimulation leads.

In some medical devices that deliver electrical stimulation therapy, therapeutic efficacy may change as the patient changes posture states. In general, a posture state may refer to a patient posture or a combination of patient posture and patient activity. For example, some posture states, such as upright, may be sub-categorized as upright and active or upright and inactive. Other posture states, such as lying down posture states, may or may not have an activity component. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. To maintain therapeutic efficacy, it may be desirable to adjust therapy parameters based on different postures and/or activities engaged by the patient. A therapy system may adjust therapy by modifying values for one or more therapy parameters, e.g., by specifying adjustments to a specific therapy parameter or by selecting different therapy programs or groups of programs that define different sets of therapy parameter values.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device employs a posture state detector that detects the patient posture state. The medical device adjusts therapy parameters in response to different posture states, which are determined with the posture state detector. Therapy adjustments in response to different posture states may be fully automatic, semi-automatic in the sense that a user may provide approval of proposed changes, or user-directed in the sense that the patient may manually adjust therapy based on the posture state indication.

In general, the disclosure describes medical devices, systems and techniques related to the delivery of therapy to a patient by a medical device. The therapy may include electrical stimulation therapy or other therapies. A medical device may be configured to monitor posture state of patient and/or patient therapy adjustments and, in some examples, deliver therapy to a patient according to the detected posture state of the patient. The delivery of therapy to a patient by a medical device according to the detected patient posture state may generally be referred to as posture-responsive therapy, and may include detecting the posture state of a patient, e.g., via one or more posture sensors, and adjusting the value of one or more therapy parameters based on the detected patient posture state.

A medical device may monitor the posture state of a patient over a period of time during which posture-responsive therapy is not delivered to a patient. For example, during such a time period, a medical device may deliver therapy to a patient albeit on a non-posture responsive basis, i.e., the therapy is not delivered according to the detected patient posture state. Alternatively, a patient may not receive therapy in general during the time period in which the patient posture state is monitored by the medical device. The period of time may include a period of time prior to that of period when a patient receives posture-responsive therapy, a period of time after the termination of posture-responsive therapy, or any combination thereof. Additionally or alternatively, a medical device may monitor the number of therapy adjustments made by a patient over a period of time during which posture-responsive therapy is not delivered to a patient. For example, during such a time period, a medical device may deliver therapy to a patient albeit on a non-posture responsive basis, i.e., the therapy is not delivered according to the detected patient posture state.

By monitoring the patient posture state and/or patient therapy adjustments, the medical device may gather patient data that includes one or more of posture state data indicative of the patient posture state during the time period when the patient was not receiving posture-responsive therapy and therapy adjustment information indicative of patient therapy adjustments made during the time period when the patient was not receiving posture-responsive therapy. Using the patient data gathered during that time period, baseline patient information may then be generated. In some examples, the baseline patient information may include baseline postures state information, such as, e.g., baseline proportional posture information, baseline sleep quality information, or baseline posture state transition information. Alternatively or additionally, the baseline patient information may include baseline therapy adjustment information, such as, e.g., the number of therapy adjustments made by patient over all or a portion of the time period.

The generated baseline patient information may then be compared to patient information that has been generated based on patient data gathered over a time period during which the patient received posture-responsive therapy from a medical device. In this manner, the baseline patient information may used as a reference point to evaluate one or more aspects of the posture-responsive therapy. For example, a medical device may present such information to a user, such as, a patient or clinician, so the user may evaluate the efficacy of one or more aspects of therapy in terms of the difference between patient posture state behavior and/or patient therapy adjustments before delivery of posture-responsive therapy versus a patient posture state behavior and/or patient therapy adjustments during a time period in which posture-responsive therapy is delivered to the patient. In view of the comparison of the baseline patient information to the patient information corresponding to a posture-responsive time period, the user may make an adjustment to one or more aspects of the posture-responsive therapy. In other examples, a medical device may automatically or semi-automatically adjust to one or more aspects of the posture-responsive therapy based on the comparison of the baseline patient information to the patient information corresponding to a posture responsive time period.

Accordingly, the generation and use of baseline patient information as described in this disclosure may provide a mechanism to evaluate the efficacy of posture-responsive therapy to a clinician or patient, and/or aid a clinician or IMD in adjusting therapy parameter values to improve therapeutic efficacy. Symptoms caused by many different diseases, disorders or conditions, e.g., chronic pain, tremor, Parkinson's disease, epilepsy, urinary or fecal incontinence, sexual dysfunction, obesity, or gastroparesis, can affect the postures and activities in which the patient chooses to engage. By monitoring the patient's posture, activity and/or therapy adjustments during a time period when the patient is not receiving posture-responsive therapy and comparing it to the patient's posture, activity and/or therapy adjustments during a time period when the patient is receiving posture-responsive therapy, a user, e.g., a clinician, may be able to objectively measure the influence that the delivery of posture-responsive therapy has had on a patient with respect to the patient's posture, activity, and/or occurrences of therapy adjustments.

In some examples, a medical device coupled to a patient may be capable of monitoring the posture state of a patient. For example, an implantable medical device (IMD) implanted within the patient may include a posture state module containing a posture state sensor capable of sensing the posture state of the patient. As another example, an external medical device that includes a posture state module containing posture state sensor capable of sensing the posture state of the patient may be temporarily attached to a patient device to monitor the patient's posture state. The external device may also be configured to deliver stimulation to a patient during a trial period or simply an external monitoring device affixed to a patient for the primary purpose of monitoring the patient's posture state. Furthermore, the IMD or external device may be configured to monitor therapy adjustments made by a patient.

In each case, the IMD or external medical device may monitor the posture state of a patient and/or patient therapy adjustments over a time period during which the patient is not receiving posture-responsive therapy. The posture state of patient may include a specific posture of the patient and/or the specific activity conducted by the patient. After the patient posture state is sensed or detected, the posture state may be stored within the memory of the IMD, external device, or other device for later retrieval and review. The IMD may store each different posture state engaged by the patient, the posture duration of each posture state, the transition between each posture state as the patient moves, or any other posture state data derived from the posture state sensor. Similarly, the IMD or other device may detect therapy adjustments made by a patient, which may then by stored within the memory of the detecting device or other device for later retrieval and review. In this manner, the IMD or other device may store posture state data and/or therapy adjustment data for retrieval to generate baseline patient information.

As described above, the baseline patient information may be compared to patient information based on patient data corresponding to a time period in which posture-responsive therapy was delivered. The patient data may include posture state data indicative of the posture state of the patient during the posture-responsive therapy time period and/or therapy adjustment data indicative of therapy adjustments made by the patient during the posture-responsive time period. The patient information generated based on patient data from the time period in which posture-responsive therapy was delivered to the patient may generally be referred to as posture-responsive patient information. During the posture-responsive therapy time period, an IMD detects the posture state of a patient and delivers therapy according to the detected patient posture state. Delivery of therapy according to the detected patient posture state may include adjusting the value of one or more therapy parameters based on the detected patient posture state. Furthermore, during the posture-responsive therapy time period, an IMD may receive one or more therapy adjustments from a patient, e.g., to adjust one or more parameters of the therapy being delivered based on the patient posture state.

FIG. 1A is a schematic diagram illustrating an implantable stimulation system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable SCS system for purposes of illustration, but without limitation as to other types of medical devices.

As shown in FIG. 1A, system 10 includes an IMD 14, external sensing device 15, and external programmer 20 shown in conjunction with a patient 12, who is ordinarily a human patient. In the example of FIG. 1A, IMD 14 is an implantable electrical stimulator that delivers SCS, e.g., for relief of chronic pain or other symptoms. Again, although FIG. 1A shows an IMD, other examples may include an external stimulator, e.g., with percutaneously implanted leads. In some examples, the external stimulator may be configured to deliver stimulation therapy to patient 12 on a temporary basis. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 12 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) coupled to IMD 14. Alternatively, as mentioned above, leads 16 may be implanted and coupled to an external stimulator, e.g., through a percutaneous port. In some cases, an external stimulator is a trial or screening stimulation that used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms (e.g., pain) or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target tissue. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to avoid causing patient 12 additional pain or unusual sensations resulting from the increased compression near electrodes of leads 16. The additional pain or unusual sensations may be considered undesirable side effects that undermine overall efficacy.

IMD 14 includes a posture state module that detects the patient posture state. When posture-responsive therapy is activated, IMD 14 automatically adjusts stimulation according to the detected posture state. The patient posture and activity level can, but need not include an activity component. Example posture states may include "Upright," "Upright and Active," "Lying Down," and so forth. IMD 14 includes a posture responsive therapy mode that, when activated, results in adjustment of one or more stimulation parameter values based on a detected posture state. The posture responsive therapy may help mitigate changes in the efficacy of therapy attributable to patient posture changes. For example, the posture state module may include one or more accelerometers that detect when patient 12 occupies a posture state for which it is appropriate to decrease the stimulation amplitude, e.g., when patient 12 lies down. IMD 14 may automatically reduce stimulation amplitude upon detecting patient 12 is lying down, thereby eliminating the need for patient 12 to manually adjust the therapy, which may be cumbersome. In addition, automatic adjustment of stimulation parameters based on a detected patient posture may also provide more responsive therapy because IMD 14 may detect a change in patient posture and modify therapy parameters faster than patient 12 may be able to manually modify the therapy parameter values.

Many other examples of reduced efficacy due to increase coupling or decreased coupling of stimulation energy to target tissue may occur due to changes in posture and/or activity level associated with patient posture state. To avoid or reduce possible disruptions in effective therapy due to posture state changes, IMD 14 includes a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 do not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

IMD 14 may also deliver therapy to patient 12 on a non-posture responsive basis. In general, when posture-responsive therapy is not activated for IMD 14, IMD 14 may deliver therapy to patient 12 but without regard to the detected posture state of patient 12. During that time, for example, while IMD 14 may deliver stimulation therapy to patient 12 according to one or more therapy groups or programs, IMD 14 does not change program group, program, stimulation amplitude, pulse width, pulse rate, and/or one or more other parameters, groups or programs in response to the detected posture state of patient 12 to maintain therapeutic efficacy. For example, IMD 14 may not detect the posture state of patient 12 when posture-responsive therapy is not activated or, alternatively, IMD 14 may detect the posture state of patient 12 but not adjust the therapy according to the detected patient postures state.

As shown in FIG. 1, system 10 also includes external sensing device 15. Similar to that of IMD 14, external sensing device may include a posture state module capable of detecting the posture state of patient 12. Accordingly, in some examples, system 10 may include external sensing device 15 in addition to IMD 14, to monitor the posture state of patient 12. In some examples, external sensing device 15 may be configured to be temporarily affixed to patient 12, e.g., in the form of an adhesive patch similar to that of an adhesive bandage, such that the posture state of patient 12 can be monitored without requiring implant IMD 14 to be implanted within patient 12.

External sensing device 15 may be utilized to monitor the posture state of patient 12 during a time period in which patient 12 is not receiving posture-responsive therapy from IMD 14. For example, External sensing device 15 may be particularly suited to monitor the posture state of patient 12 during time period in which IMD 14 has not yet been implanted in patient 12 and, therefore, at time in which IMD 14 is not able to monitor the posture state of patient 12. However, in some examples, external sensing device may also monitor the posture state of patient 12 after IMD 14 has been implanted in patient 12. For example, external sensing device 15 may monitor the posture state of patient 12 during a time period in which patient 12 is receiving posture-responsive therapy from IMD 14, or even a time period during which patient 12 is not receiving posture-response therapy but after IMD 14 has been implanted in patient 12.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

As will be described in greater detail below, IMD 14, external device 15, and/or any other suitable device may monitor the posture state of patient 12 and/or therapy adjustments made by patient 12 during a time period in which IMD 14 does not deliver posture-responsive therapy to patient 12. As referred to herein, patient data may include at least one of posture state data indicative of the plurality of posture states of patient during a respective time period and therapy adjustment date indicative of patient therapy adjustments during a respective time period. Using the patient data from the time period when posture-responsive therapy was not delivered to patient 12, IMD 14, external programmer 20 or any other suitable device may generate baseline patient information for patient 12. The baseline patient information may then be compared to posture-responsive patient information, i.e., patient information generated based on patient data during to a time period in which IMD 14 delivered posture-responsive therapy to patient 12. The comparison of the baseline patient information to the posture-responsive patient information may allow a user, such as a clinician or patient, or IMD 14 to evaluate the efficacy of the posture-responsive therapy delivered to patient 12 via IMD 14.

External programmer 20 may present one or more aspects of the comparison of baseline patient information to posture-responsive patient information to a user. In some examples, external programmer 20 acquires patient data indicative of patient postures state and/or patient therapy adjustments during a time period in which patient 12 was not receiving posture-responsive therapy from IMD 14 or external sensor 15, and then generates baseline patient information based on the acquired patient data. In other examples, IMD 14 or external sensor 15 acquires the patient data and generates the baseline patient information based on the patient data, which is then communicated to external programmer 20 for presentation to a user. The baseline patient information may include baseline sleep quality information, baseline proportional posture information, therapy adjustment information, or other information that objectively indicates how patient 12 has been moving or adjusting therapy during the time period that IMD 14 is not delivering posture responsive therapy to patient 12. External programmer 20 may present one or more aspects of the comparison of baseline patient information and the posture-responsive patient information graphically as a chart or graph, numerically, or some combination thereof.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

Figure 1B:
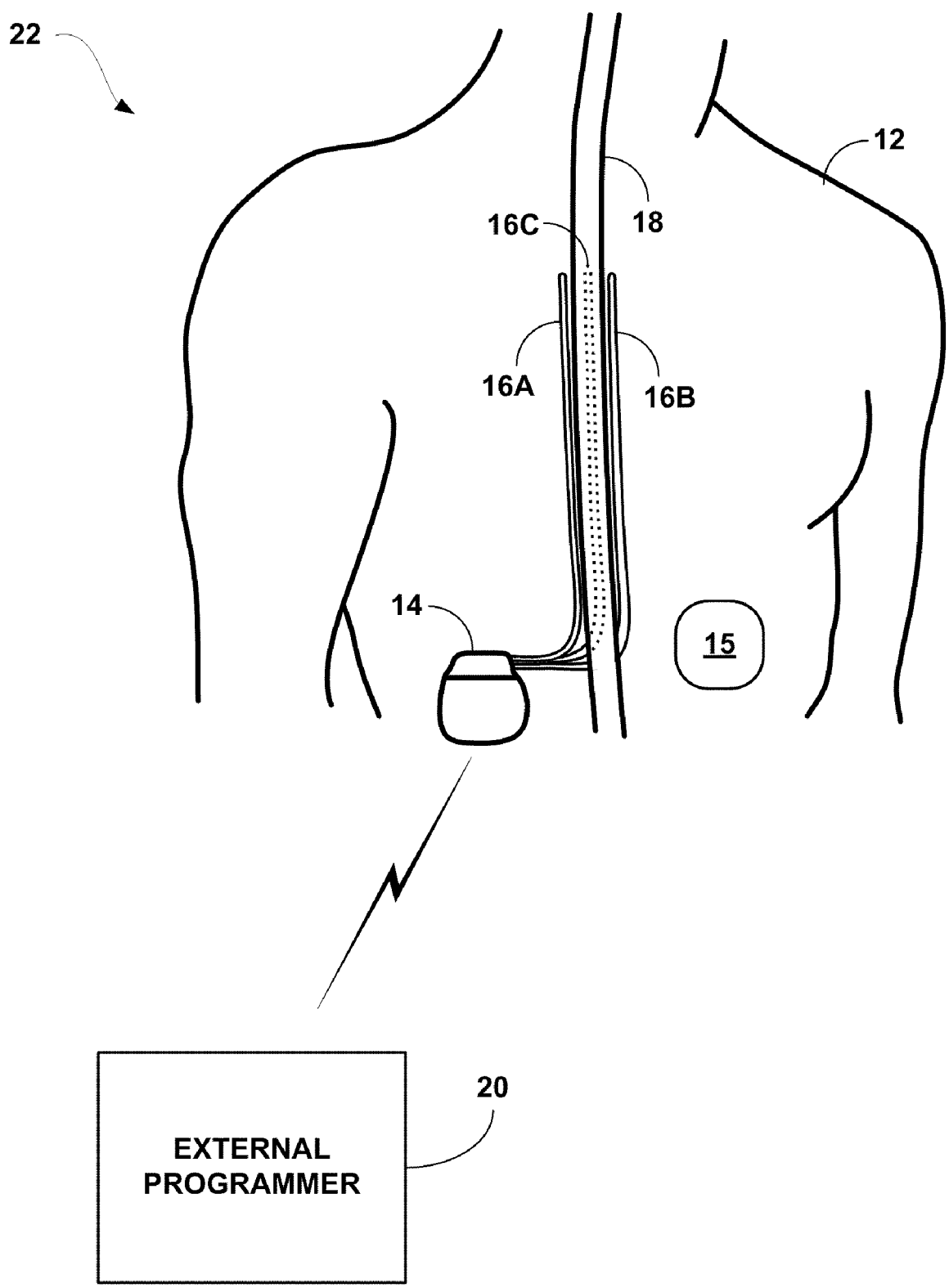
FIG. 1B is a conceptual diagram illustrating an example implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy.

In some examples, leads 16A and 16B each include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
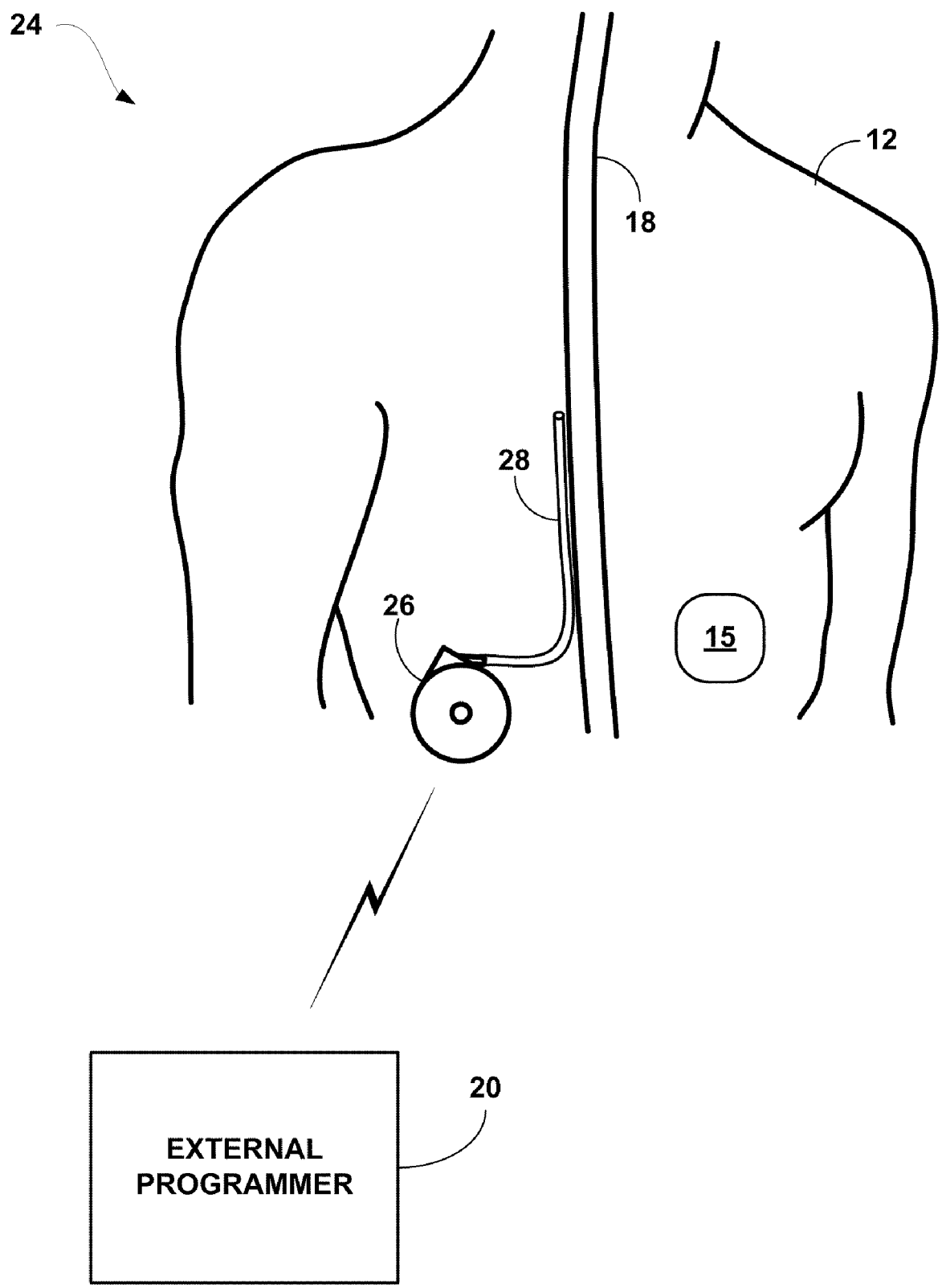
FIG. 1C is a conceptual diagram illustrating an example implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of one or more therapeutic agents instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter that to deliver a therapeutic agent to patient 12, e.g., in the same manner as catheter 28. Alternatively, the percutaneous catheter can be coupled to catheter 28, e.g., via a fluid coupler. In other examples, IMD 26 may include both electrical stimulation capabilities as described in IMD 14 (FIG. 1A) and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 includes a posture state module that monitors the patient 12 posture state and adjusts therapy accordingly when IMD 26 is activated for posture-responsive therapy. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
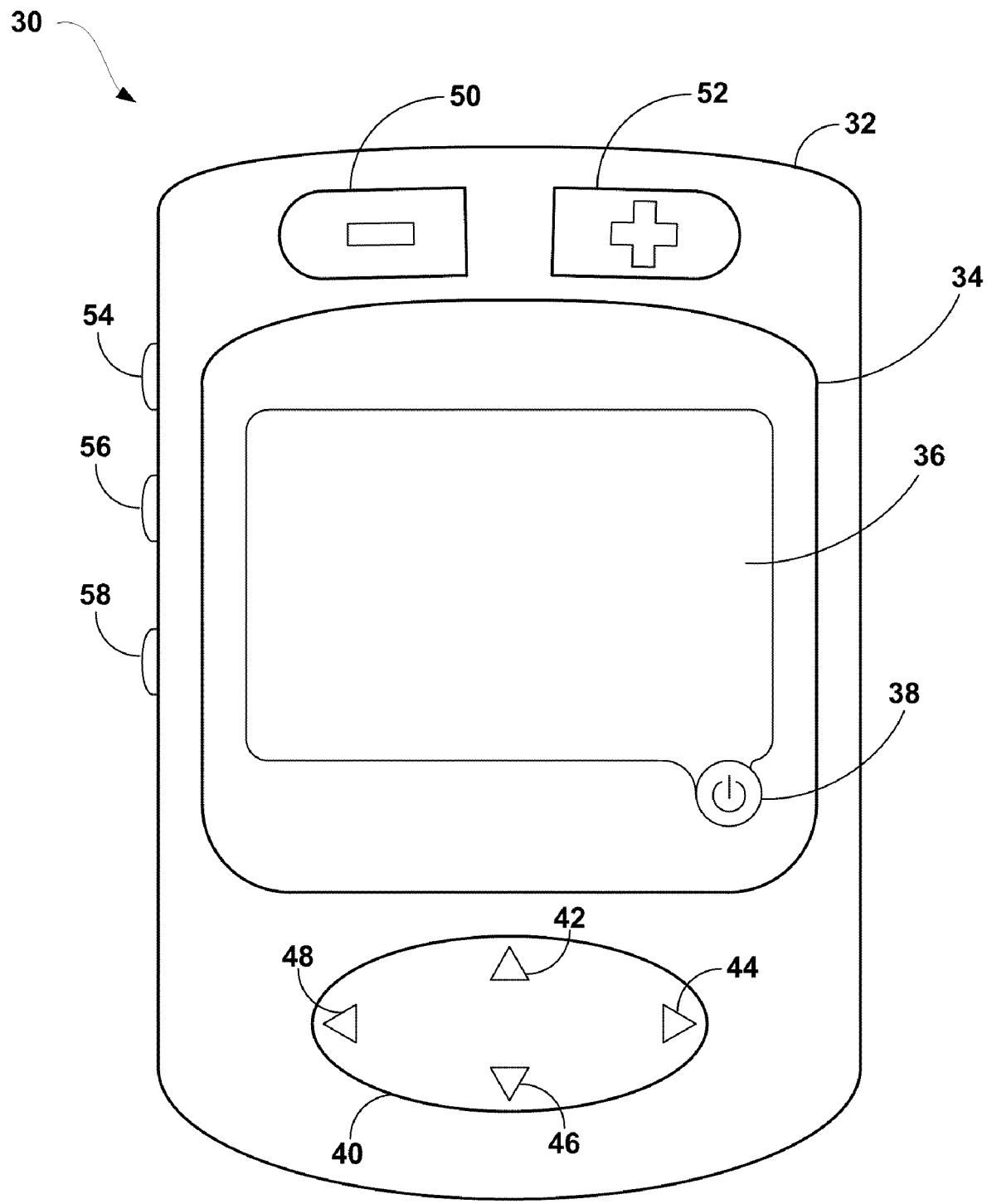
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. Patient programmer 30 may be used to present a comparison of baseline patient information and posture-responsive patient information to patient 12. Patient programmer 30 is protected by housing 32, which encloses circuitry necessary for patient programmer 30 to operate. Patient 12 may use programmer 30 to make adjustments to therapy being delivered by IMD 14.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In some examples, pressing the middle of control pad 40 selects any items highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy.

Decrease button 50 and increase button 52 provide an input mechanism for patient 12. In general, activation of decrease button 50 (e.g., by pressing button 50) decreases the value of a highlighted stimulation parameter every time the decrease button is pressed. In contrast, activation of increase button 52 increases the value of a highlighted stimulation parameter one step every time the increase button is pressed. While buttons 50 and 52 may be used to control the value of any stimulation parameter, buttons 50 and 52 may also control patient feedback input. When either button 50 or 52 is selected, patient programmer 30 may initialize communication with IMD 14 or 26 to change therapy accordingly.

When depressed by patient 12, stimulation ON button 54 directs programmer 30 to generate a command for communication to IMD 14, where the command instructs IMD 14 to turn on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
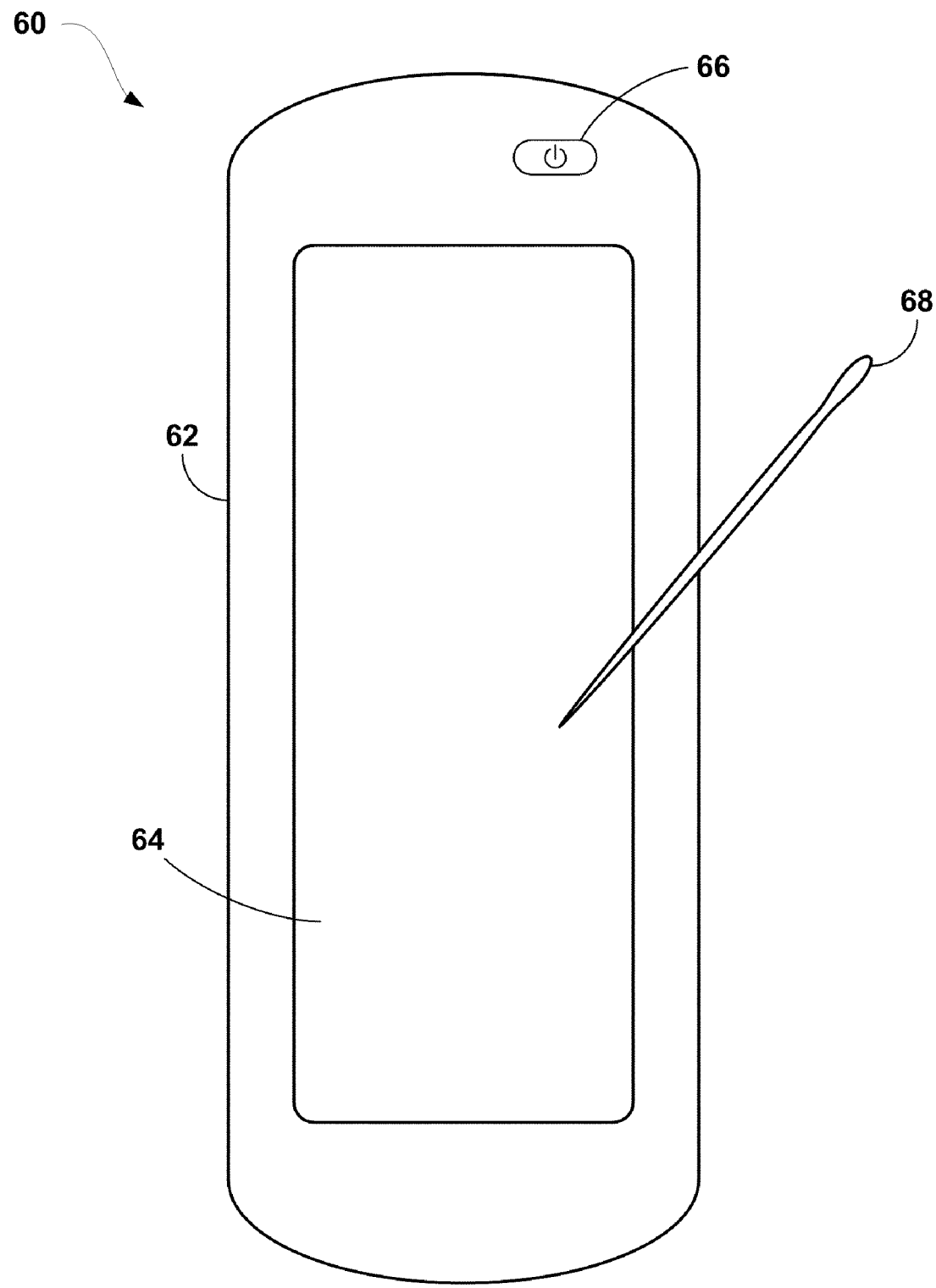
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an IMD. Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. In addition, clinician programmer 60 may be used to present one or more aspects of the comparison between baseline patient information and posture-responsive patient information to a clinician. This information may allow a clinician to evaluate the efficacy of posture-responsive therapy to patient 12, as well as monitor patient progress relative to the baseline patient information. Clinician programmer 60 is protected by housing 62, which encloses circuitry necessary for clinician programmer 60 to operate.

Clinician programmer 60 is used by the clinician or other user to modify and review therapy to patient 12. The clinician may define each therapy parameter value for each of the programs that define stimulation therapy. The therapy parameters, such as amplitude, may be defined specifically for each of the posture states that patient 12 will be engaged in during therapy. In addition, the clinician may use clinician programmer 60 to define each posture state of patient 12 by using the posture cones described herein or some other technique for associating posture state sensor output to the posture state of patient 12.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation therapy (e.g., selecting stimulation parameter values), modify programs or groups, retrieve stored therapy data, retrieve patient information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Clinician programmer 60 may also allow the clinician to objectively evaluate the posture states of patient 12 during one or more time period or patient therapy adjustments by monitoring the posture states of patient 12 during the one or more time periods and/or patient therapy adjustments made during the one or more time periods. The posture and activity of patient 12 and patient therapy adjustments may be stored in IMD 14 as patient data and may be presented by clinician programmer 60 in the form of baseline and posture-responsive patient information. The patient information may be sleep quality information, proportional posture information, posture state adjustment information, patient therapy adjustment information or other information that includes objective data related to the frequency and duration of the posture states occupied by patient 12 and/or frequency and number of patient therapy adjustments. This information may be presented in an organized graphical and/or numerical manner for quick reference by the clinician.

In some examples, clinician programmer 60 may not store any of the posture state data used to generate the baseline and posture-responsive patient information. Each time that the clinician desires to view the objective information related to the posture states and/or therapy adjustments, clinician programmer 60 may need to acquire all or some of the patient data from IMD 14 and/or external sensing device 15. In other examples, clinician programmer 60 may store patient data from IMD 14 and/or external sensing device 15 each time that clinician programmer 60 communicates with IMD 14. In this manner, clinician programmer 60 may only need to acquire the patient data stored in IMD 14 and/or external sensing device 15 since the previous communication with IMD 14 and/or external sensing device 15. Of course, clinician programmer 60 may not require all patient data stored by IMD 14 and/or external sensing device 15. In some embodiments, only the patient data stored during desired time intervals, or relating to particular patient information, may be used to generate the baseline and posture-responsive patient information. In some cases, IMD 14 and/or external sensing device 15 may generate the patient information based on the patient data, and then communicate the generated patient information to programmer 60 for presentation to a user in one form or another.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4A:
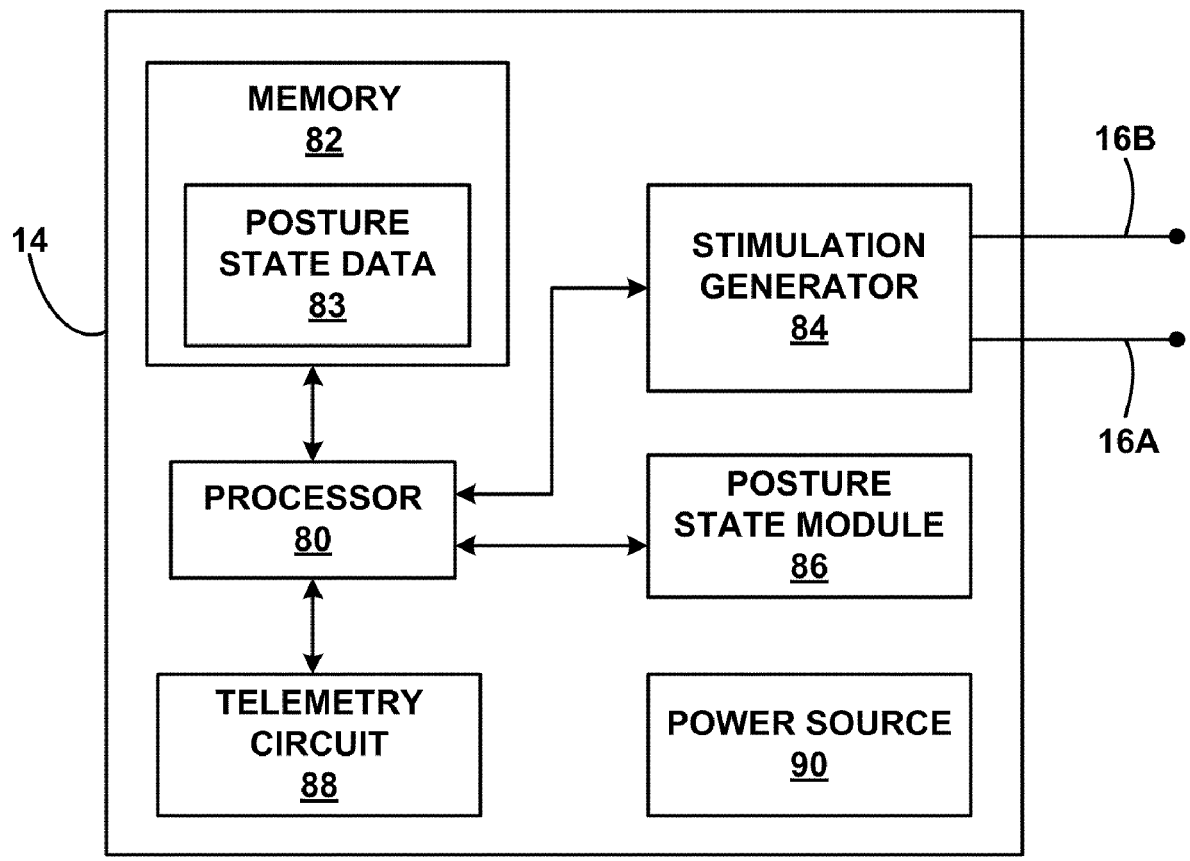
FIGS. 4A and 4B are functional block diagrams illustrating various components of an example implantable electrical stimulator and an example external sensing device, respectively.

FIG. 4A is a functional block diagram illustrating various components of an IMD 14. In the example of FIG. 4A, IMD 14 includes a processor 80, memory 82, stimulation generator 84, posture state module 86, telemetry circuit 88, and power source 90. The stimulation generator 84 forms a therapy delivery module.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information (e.g., posture state definitions, information associating posture states with therapy programs, and the like), posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

As shown in FIG. 4A, memory 82 may store patient data 83 that is indicative of posture state of patient 12 and/or patient therapy adjustments. For example, patient data 83 may include information regarding the posture state of patient 12 detected via posture module 86. In some examples, patient data 83 may include raw or filtered posture sensor signal data that may later be analyzed (e.g., by programmers 30, 60) using one or more posture state detection techniques, such as, e.g., one or more of the techniques described below with regard to FIGS. 8A-8C, to determine the posture state of patient 12 indicated by the posture sensor signal data. As another example, patient data 83 may include information regarding patient therapy adjustments.

Patient data 83 may also include information that may be used to differentiate between whether specific patient data corresponds to a time period when IMD 14 delivered posture-responsive stimulation to patient 12, or a time period when patient was not receiving posture responsive therapy from IMD 14. For example, patient data 83 may include a general indication of whether or not IMD 14 was in posture-responsive therapy mode when the patient data was sensed. Additionally or alternatively, patient data 83 may include a particular time stamp indicating the time that posture sensor data was sensed or posture state was detected, or when a patient therapy adjustment was received. This time information may be correlated with one or more therapy records to determine whether IMD 14 was delivering posture-responsive therapy active at the time. The time information may also be useful for generating and comparison of the baseline patient information and posture-responsive patient information.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or continuous waveforms and, in some examples, switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, when IMD 14 is activated for delivery of posture-responsive therapy, such stimulation parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state.

Processor 80 also may control telemetry circuit 88 to send and receive information to and from external programmer 20. For example, telemetry circuit 88 may send information to and receive information from patient programmer 30.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4A, posture state module 86 includes one or more accelerometers, such as three-axis accelerometers, capable of detecting static orientation or vectors in three-dimensions. Example accelerometers include a micro-electro-mechanical accelerometer. In other examples, posture state module 86 may alternatively or additionally include one or more gyroscopes, piezoelectric crystals, pressure transducers or other sensors to sense the posture state of patient 12. Posture state data generated by posture state module 86 and processor 80 may correspond to an activity and/or posture undertaken by patient 12 or a gross level of physical activity, e.g., activity counts based on footfalls or the like. Posture state data may be indicative of the posture state of patient 12.

Posture state data from posture state module 86 may be stored in memory 82 for later review by a clinician, used to adjust therapy, present a posture state indication to patient 12 (e.g., via patient programmer 30), or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

As described herein, the posture state data indicative of patient posture state may be stored to be later used to generate baseline patient information and/or posture-responsive patient information. Memory 82 may store all of the posture state data detected during therapy or use of IMD 14, or memory 82 may periodically offload the posture state data to clinician programmer 60 or a different external programmer 20 or device. In other examples, memory 82 may reserve a portion of the memory, e.g., patient data 83, to store recent posture state data easily accessible to processor 80 for analysis. In addition, older posture state data may be compressed to require less memory until later needed by external programmer 20 or processor 80.

A posture state parameter value from posture state module 86 that is indicative of the posture state may constantly vary throughout the day of patient 12. However, a certain activity (e.g., walking, running, or biking) or a posture (e.g., standing, sitting, or lying down) may include multiple posture state parameter values from posture state module 86. Memory 82 may include definitions for each posture state of patient 12. In one example, the definition of each posture state may be illustrated as a cone in three-dimensional space. Whenever the posture state parameter value, e.g., a vector, from the three-axis accelerometer of posture state module 86 resides within a predefined cone, processor 80 indicates that patient 12 is in the posture state of the cone. In other examples, posture state parameter value from the 3-axis accelerometer may be compared to a look-up table or equation to determine the posture state in which patient 12 currently resides.

Posture-responsive stimulation therapy may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 14 to, for example, depress one or more keys of patient programmer 30 multiple times during the patient posture state to maintain adequate symptom control. In some examples, patient 12 may eventually be able to enjoy posture-responsive stimulation therapy without the need to continue making changes for different postures via patient programmer 30. Instead, patient 12 may transition immediately or over time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion. This activity may involve a level, direction of motion, or acceleration of the patient.

One method for determining the patient activity is by determining an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

IMD 14 wirelessly communicates with external programmer 20, e.g., patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 4B:
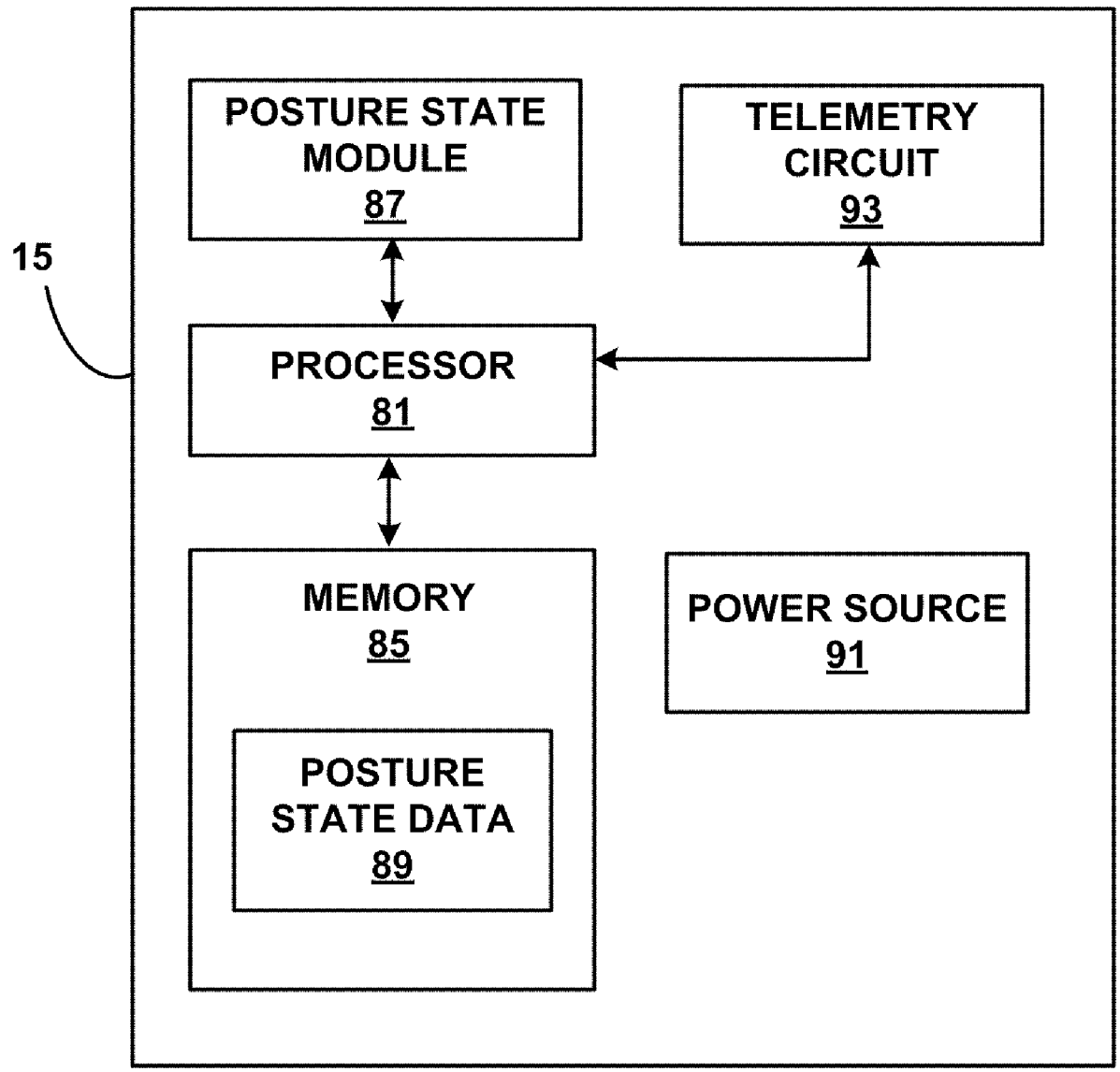

FIG. 4B is a functional block diagram illustrating various component of an external sensing device 15. In the example, of FIG. 4B, external sensing device includes processor 81, memory 85, posture state module 87, power source 91 and telemetry circuit 93. External sensing device 15 may operate substantially similar to that of IMD 14 of FIG. 4A. However, unlike IMD 14, external sensing device 15 does not include a stimulation generator and is not configured to delivery stimulation therapy to patient 12. Rather, external sensing device 15 is configured to monitor the posture state of patient 12 via posture state module 87.

External sensing device 15 may be temporarily affixed to patient 12 to monitor the posture state of patient 12 over a period of time. As described above, external sensing device 15 may be configured to the affixed to patient 12 in a manner that allows external sensing device 15 to accurately monitor the posture state of patient 12 over a period of time. For example, external sensing device 15 may be configured as an adhesive bandage or pad that may be adhered to the skin of patient 12. As another example, external sensing device 15 may be configured to be strapped to patient 12, e.g., to the wrist of a patient similar to that of a watch, or the torso of patient 12, to temporary attach external sensing device 15 to patient 12.

Similar to that of IMD 14, external sensing device 15 may monitor the postures states of patient 12 via posture state module 87 and then store the patient data 89, e.g., posture state data indicative of patient posture state, in memory 85. External sensing device 15 may be used to monitor the posture state of patient 12 over a desired period of time, including one or more time periods during which patient 12 is not receiving posture-responsive therapy from IMD 14 and/or one or more time periods during which patient 12 is receiving posture-responsive therapy from IMD 14. Although not limited to such situations, external sensing device 15 may be particularly useful for monitoring the posture state of patient 12 during periods of time in which posture state module 86 of IMD 14 is not detecting the posture state of patient 12, e.g., prior to the implantation of IMD 14 within patient 12.

Programmer 20 or other external device may periodically interrogate external sensing device 15 using telemetry circuit 93 to acquire patient data 89, e.g., posture state data, for patient 12 over any given period of time. Telemetry circuit 93 may support wired and/or wireless telemetry with programmer 20 or other external device. Using the acquired posture state data 89, programmer 20 or other external device may generate patient information, which may be either baseline patient information or posture-responsive patient information depending on whether IMD 14 was active for delivery of posture-responsive therapy to patient 12 during the time period with which the particular patient data is associated.

Figure 5:
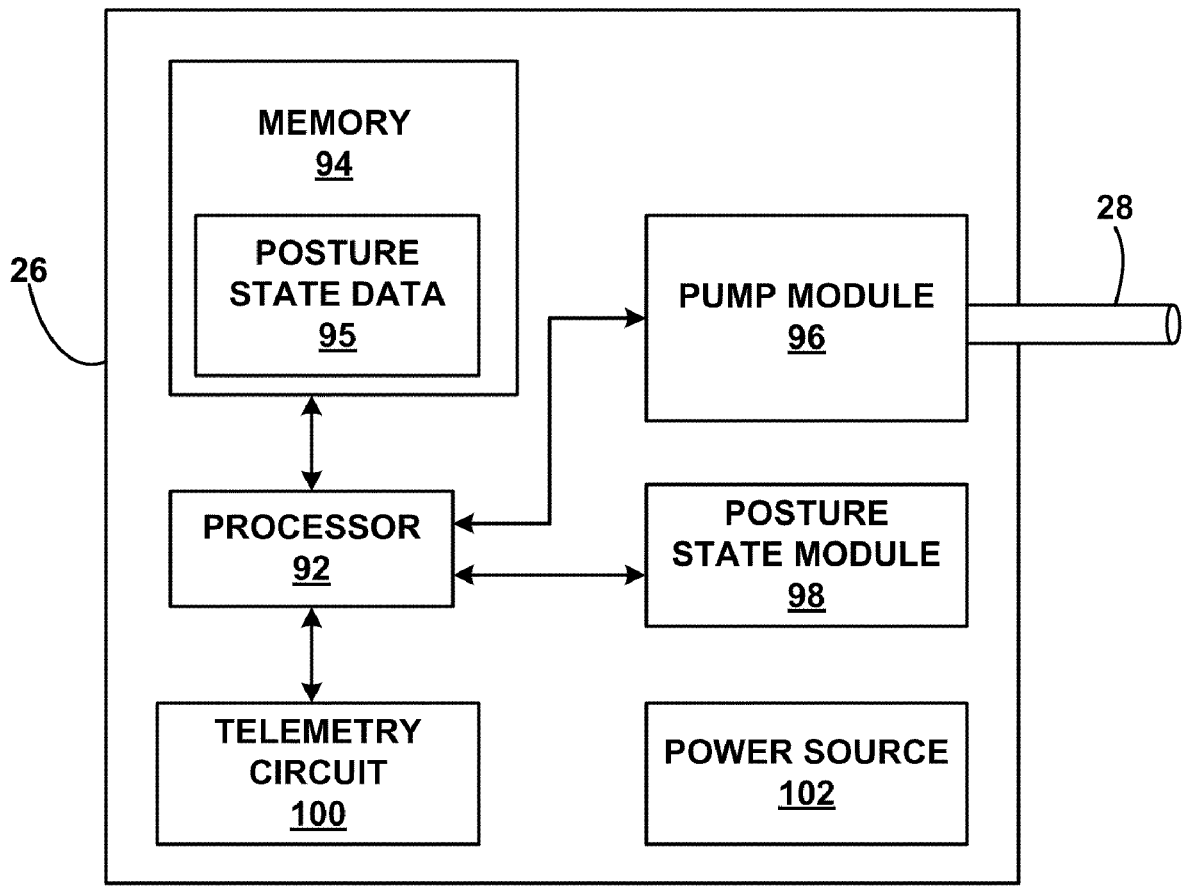
FIG. 5 is a functional block diagram illustrating various components of an example implantable drug pump.

FIG. 5 is a functional block diagram illustrating various components of an IMD 26, which delivers a therapeutic agent to patient 12. IMD 26 is a drug pump that operates substantially similar to IMD 14 of FIG. 4A, but delivers a therapeutic agent instead of electrical stimulation. IMD 26 includes processor 92, memory 94, pump module 96, posture state module 98, telemetry circuit 100, and power source 102. Memory 94 includes posture state data 95. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state data from posture state module 98 to adjust drug delivery therapy when patient 12 changes posture states, e.g., adjusts his or her posture.

Figure 6:
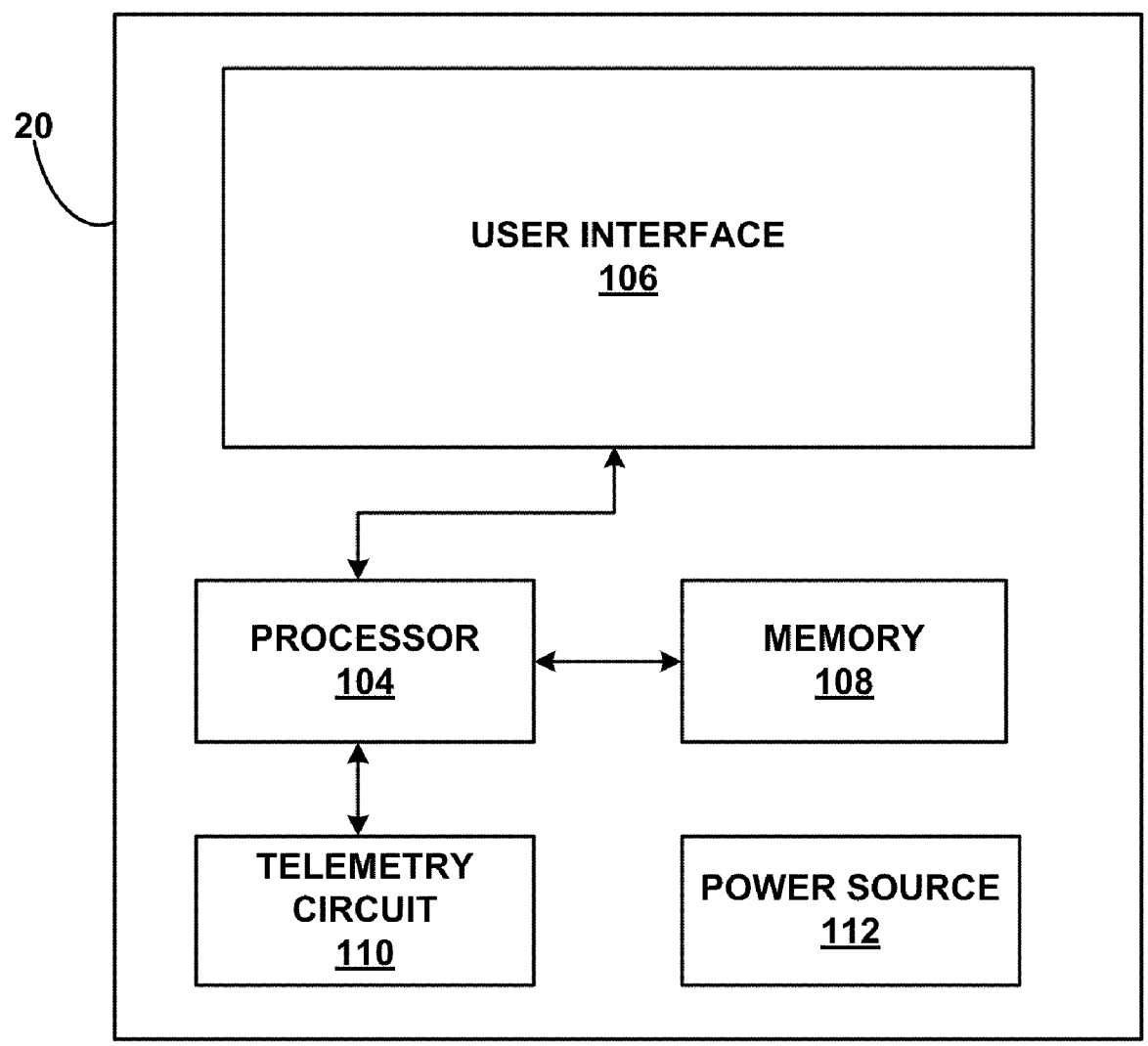
FIG. 6 is a functional block diagram illustrating various components of an example external programmer for an implantable medical device.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 includes processor 104, memory 108, telemetry circuit 110, user interface 106, and power source 112. External programmer 20 may be embodied as patient programmer 30 (FIG. 2) or clinician programmer 60 (FIG. 3).

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. Memory 108 also includes instructions for generating and delivering programming commands to IMD 14, such as a programming command that instructs IMD 14 to activate or deactivate a posture responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician, patient 12 or another user (e.g., a patient caretaker) interacts with user interface 106 in order to manually change the stimulation parameter values of a program, change programs within a group, turn posture responsive stimulation ON or OFF, view therapy information, view posture state information, or otherwise communicate with IMDs 14 or 26.

User interface 106 may include a screen and one or more input mechanisms, such as buttons as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input mechanisms for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

User interface 106 configured to present baseline patient information and posture-responsive patient information to the user. In addition to presenting text, user interface 106 may be configured to present graphical representations to the user in grayscale, color, and other visual formats. For example, in examples which the patient information includes proportional posture information, user interface 106 may be configured to present the baseline proportional posture information and posture-responsive proportional information as a graphical posture duration graphs that visually indicates the proportion of time patient 12 has been engaged in each posture state during each respective time period. User interface 106 may be able to reconfigure the displayed posture duration graph to show the percentage difference between the baseline proportional posture information and posture-responsive proportional posture information to the user. From this information, the user may be able to evaluate the efficacy of posture-responsive therapy based on a comparison of the baseline patient information to posture-responsive patient information. In some examples, the user may adjust one or more aspects of the posture-responsive therapy in view of the comparison in an attempt to improve therapeutic efficacy.

Baseline and posture-responsive patient information may be stored within memory 108 or within another data storage device, such as a hard drive, flash memory or the like. External programmer 20 may store information obtained from previously interrogating IMD 14 and/or external sensing device 15 so that that same information does not need to be retrieved from the IMD or external sensing device repeatedly, and so that IMD 14 and/or external sensing device 15 may overwrite information, if necessary, in some implementations. Hence, external programmer 20 may retrieve new information from IMD 14 and/or external sensing device 15, i.e., information that has been newly obtained since the previous interrogation, and also rely on archived information stored in the programmer or elsewhere. External programmer 20 may store the patient information in memory 108 during communication sessions with IMD 14 and/or external sensing device 15. The user may then have quick access to the patient data without first communicating to IMD 14 and/or external sensing device 15, and acquiring the patient data from IMD 14 and/or external sensing device 15 every time that the user desired to review baseline and posture responsive patient information, for example. If memory 108 does store patient information from patient 12, memory 108 may use one or more hardware or software security measures to protect the identify of patient 12. For example, memory 108 may have separate physical memories for each patient or the user may be required to enter a password to access each patient's data.

Telemetry circuit 110 allows the transfer of data to and from IMD 14, IMD 26, and/or external sensing device. Telemetry circuit 110 may communicate automatically with IMD 14 or external sensing device 15 at a scheduled time or when the telemetry circuit detects the proximity of the stimulator. Alternatively, telemetry circuit 110 may communicate with IMD 14 or external sensing device 15 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter. Telemetry circuitry 110 may additionally or alternatively support wired communication, e.g., with telemetry circuitry 93 of external sensing device 15.

Although not shown in FIG. 6, in some examples, external programmer 20 may include a charger module capable of recharging a power source, such as a rechargeable battery that may be included in power source 90 of IMD 14. Hence, in some cases, the programmer may be integrated with recharging components to form a combined programmer/recharger unit. In some examples, programmer 20 may be coupled to a separate recharging device capable of communication with IMD 14. Then, the recharging device may be able to transfer programming information, data, or any other information described herein to IMD 14. In this manner, the recharging device may be able to act as an intermediary communication device between external programmer 20 and IMD 14. The techniques described herein may be communicated between IMD 14 via any type of external device capable of communication with IMD 14.

Figure 7:
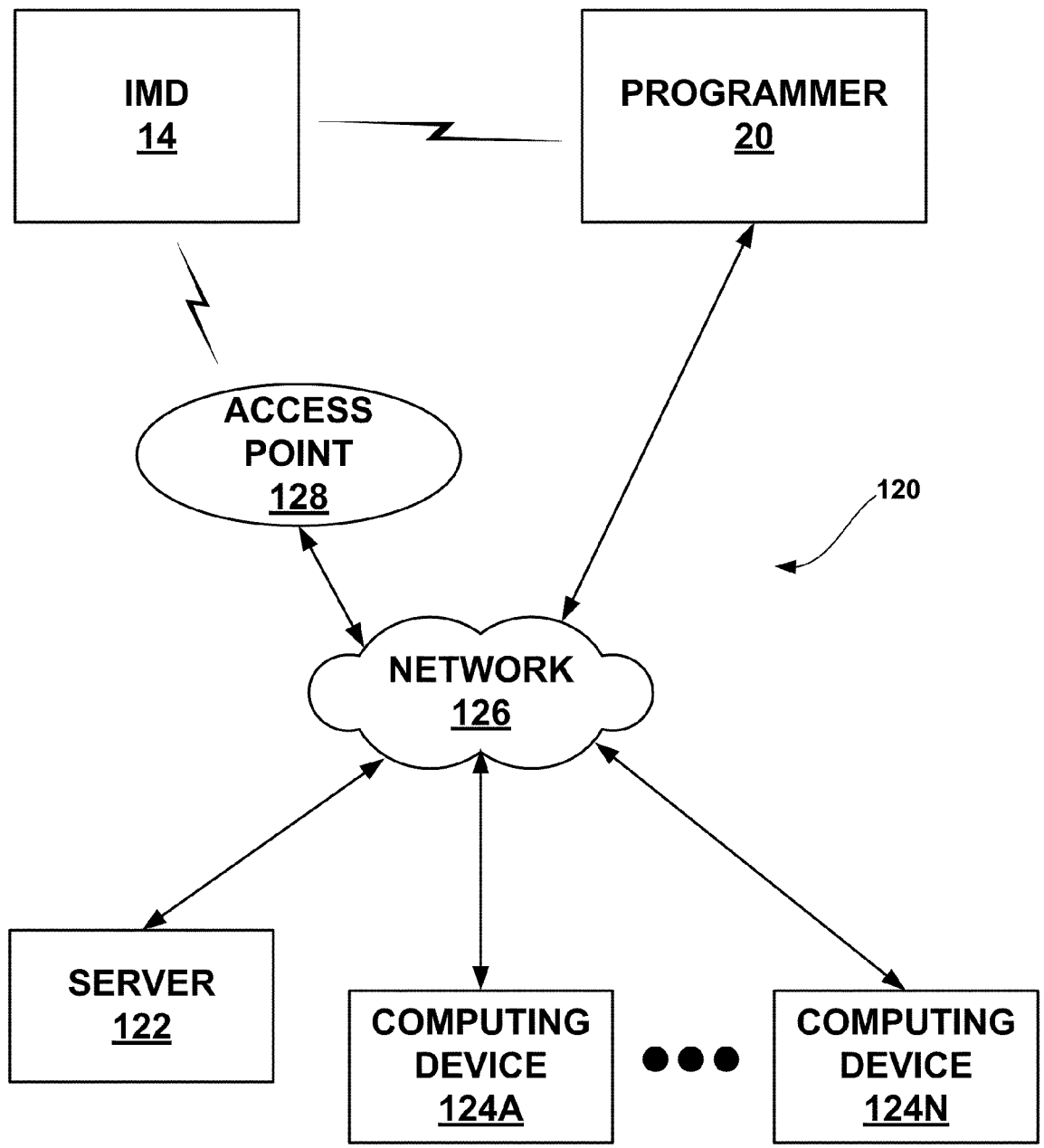
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 (FIG. 4A) to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60. Although not shown, external sensing device 15 may also be coupled to server 122 and computing device 124A-124N in a manner similar to that of IMD 14.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of patient data. For example, IMD 14 may collect sensed posture state data during posture-responsive therapy and other time periods that indicates the posture state of patient 12 and/or collect therapy adjustment information that is indicative of patient therapy adjustments. For example, the posture state data may be indicative of how patient 12 moves throughout each day, or other particular time period. In some cases, IMD 14 may directly analyze the collected data to generate baseline and/or posture-responsive patient information of patient 12, such as what percentage of time patient 12 was in each identified posture state or the number of therapy adjustments made by patient. In other cases, however, IMD 14 may send stored patient data to external programmer 20 and/or server 122, either wirelessly or via access point 128 and network 126, for remote processing and analysis. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, patient data and/or generated patient information (e.g., baseline and/or posture-responsive) may be archived by any of such devices, e.g., for later retrieval and analysis by a clinician.

In some cases, IMD 14, external programmer 20, external sensing device 15 or server 122 may process the patient data, generate patient information into a displayable posture state report, which may be displayed via external programmer 20 or one of computing devices 124A-124N. The posture state report may contain comparative data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20, external sensing device 15 or server 122. A clinician or other trained professional may review and/or annotate the posture state report, and possibly identify any problems or issues with the therapy that should be addressed.

In the manner of FIG. 7, a clinician, physician, technician, or even patient 12, may review data by comparing baseline patient information with respect to the posture states of patient 12. The comparative baseline and posture-responsive patient information may be sleep quality information or proportional posture information that reflects how patient 12 has been moving before, during, and/or after a time period during which posture-responsive therapy was delivered from IMD 14. The user may remotely monitor the progress and trends of patient 12 with respect to baseline patient information, limiting the number of times that patient 12 may need to physically visit the clinician. Comparative patient information may be displayed to patient 12 to illustrate the effectiveness of posture-responsive therapy, as well the progress of patient 12. The remote monitoring supported by system 120 may also reduce the time needed to find efficacious therapy parameters by allowing the clinician to more frequently monitor differences in posture-responsive patient information, such as, e.g., posture-responsive sleep quality information and proportional posture information, with respect to the corresponding baseline patient information. Any of the user interfaces described herein with respect to patient programmer 30 or clinician programmer 60 may also be presented via any of computing devices 124A-124N.

In some cases, server 122 may be configured to provide a secure storage site for archival of patient data or generated patient information that has been collected from IMD 14, external sensing device 15, and/or external programmer 20. Network 126 may comprise a local area network, wide area network, or global network, such as the Internet. In some cases, external programmer 20 or server 122 may assemble posture state data or generated patient information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve patient information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, external sensing device 15, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating patient information, as described in this disclosure, may be applied to IMDs that are generally dedicated to sensing or monitoring and do not include stimulation or other therapy components, such as, external sensing device 15. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
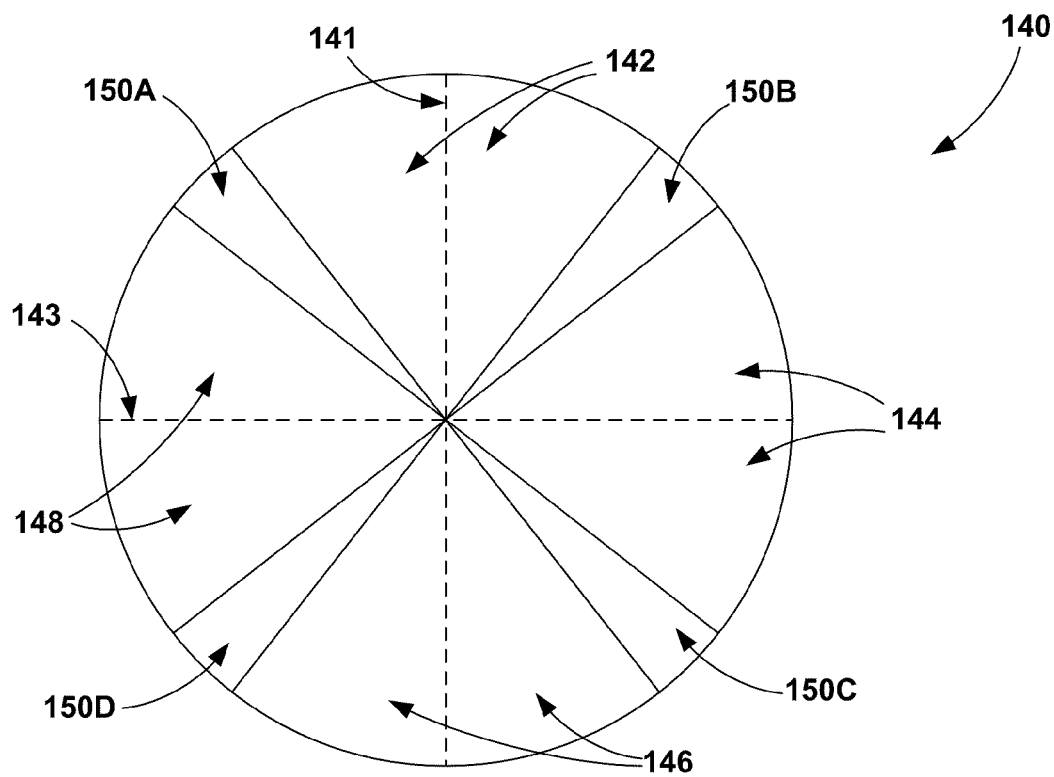
FIGS. 8A-8C are conceptual illustrations of example posture state spaces within which postures state reference data may define the posture state of a patient.
Figure 8B:
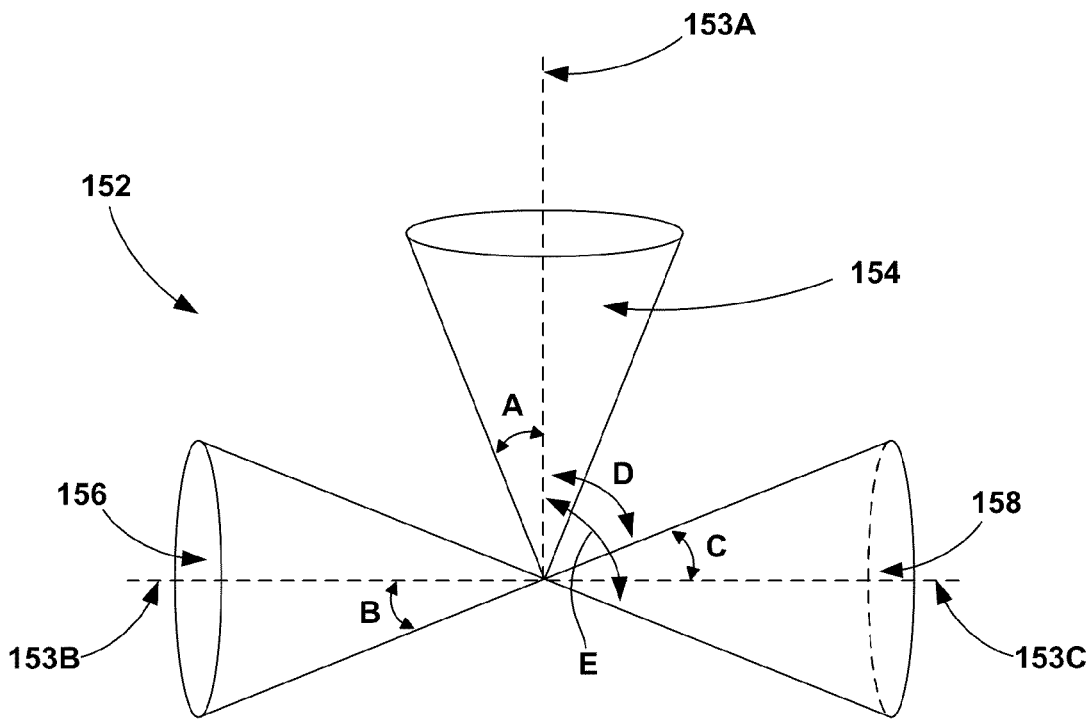
Figure 8C:
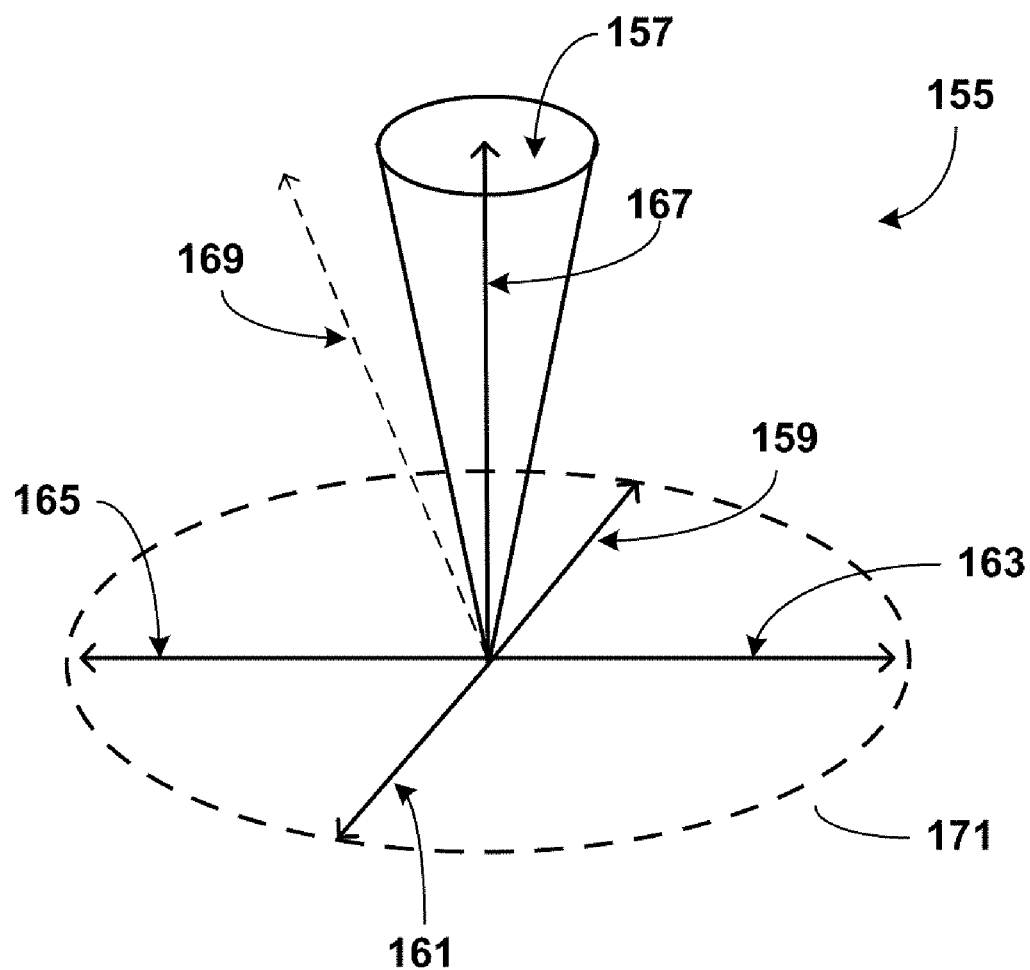

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E' may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
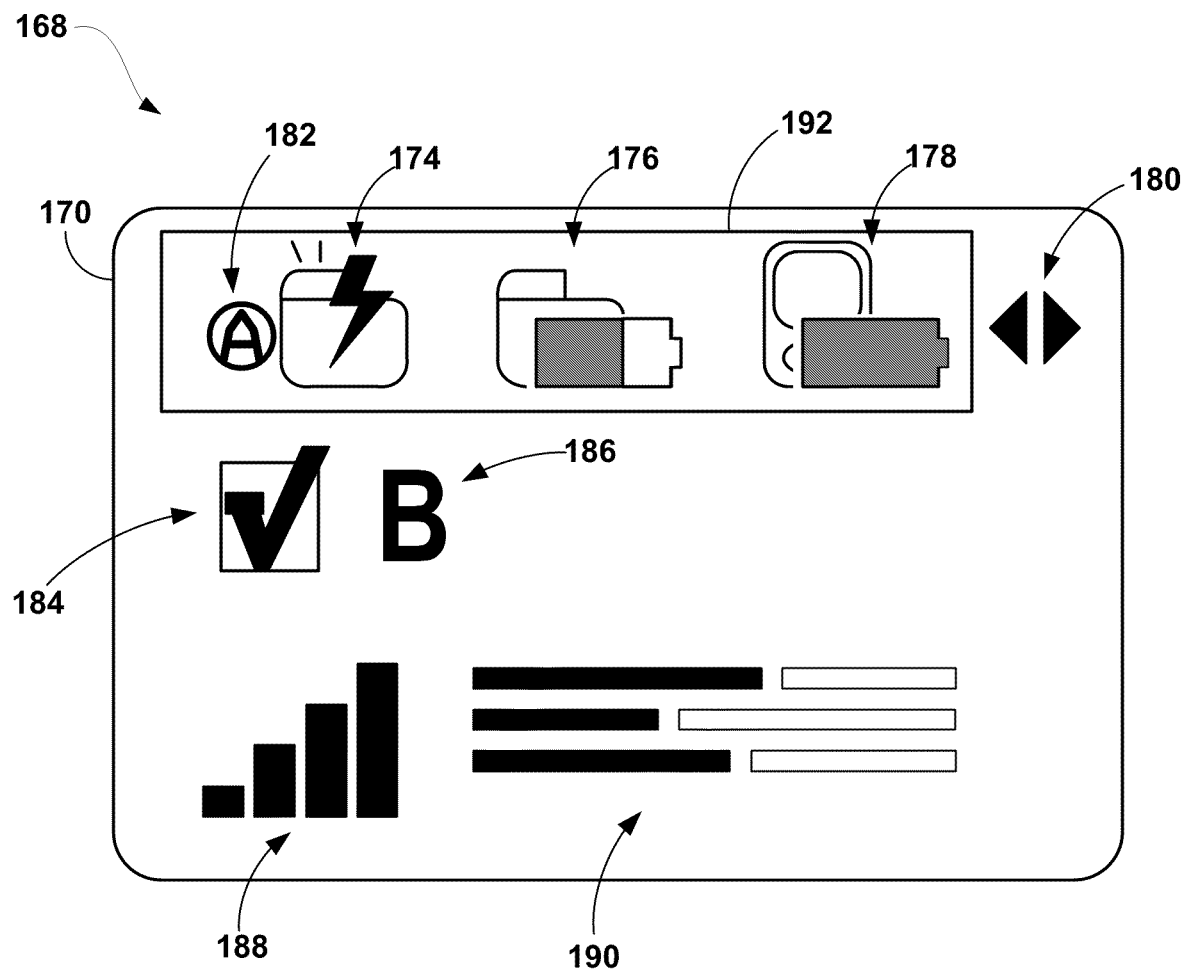
FIG. 9 is a conceptual diagram illustrating an example user interface of a patient programmer for delivering therapy information to the patient.

FIG. 9 is a conceptual diagram illustrating an example user interface 168 of a patient programmer 30 for delivering therapy information to patient 12. In other examples, a user interface similar to user interface 168 may also be presented by clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example, of screen 170, selection box 192 is positioned so that patient 12 may use arrows 44 and 48 (FIG. 2) of control pad 40 of programmer 30 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the stored program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some examples, numerical values of each program's amplitude may be show in addition to or in place of amplitude graph 190. In other examples of user interface 168 specific to drug delivery using IMD 26, amplitude graph 190 may show the flow rate of drugs or frequency of bolus delivery to patient 12. This information may be show in numerical format as well. Patient 12 may encompass group selection icon 184 with selection box 192 to scroll between the different programs of the selected group.

Automatic posture response icon 182 indicates that IMD 14 is generally activated, such that processor 80 automatically modifies therapy to patient 12 based upon the posture state detected by posture state module 86. In particular, automatic posture responsive therapy may involve adjusting one or more therapy parameter values, selecting different programs or selecting different program groups based on the detected posture state of the patient. However, automatic posture response icon 182 is not present next to group identifier 186, indicating that group "B" does not have automatic posture responsive therapy activated for any of the programs within group "B."

Some groups or individual programs in groups may support automatic posture responsive therapy. For example, automatic adjustment of one or more therapy parameter values in response to posture state indication may be selectively activated or deactivated based on settings entered by a clinician, or possibly patient 12. Hence, some programs or groups may be configured for use with posture responsive therapy while other programs or groups may not be configured for use with posture responsive therapy. In some cases, if posture responsive therapy supported by the automatic posture response feature is desired, patient 12 may need to switch therapy to a different group that has automatic posture responsive therapy activated for IMD 14 to adjust therapy according to the patient 12 posture state.

Figure 10:
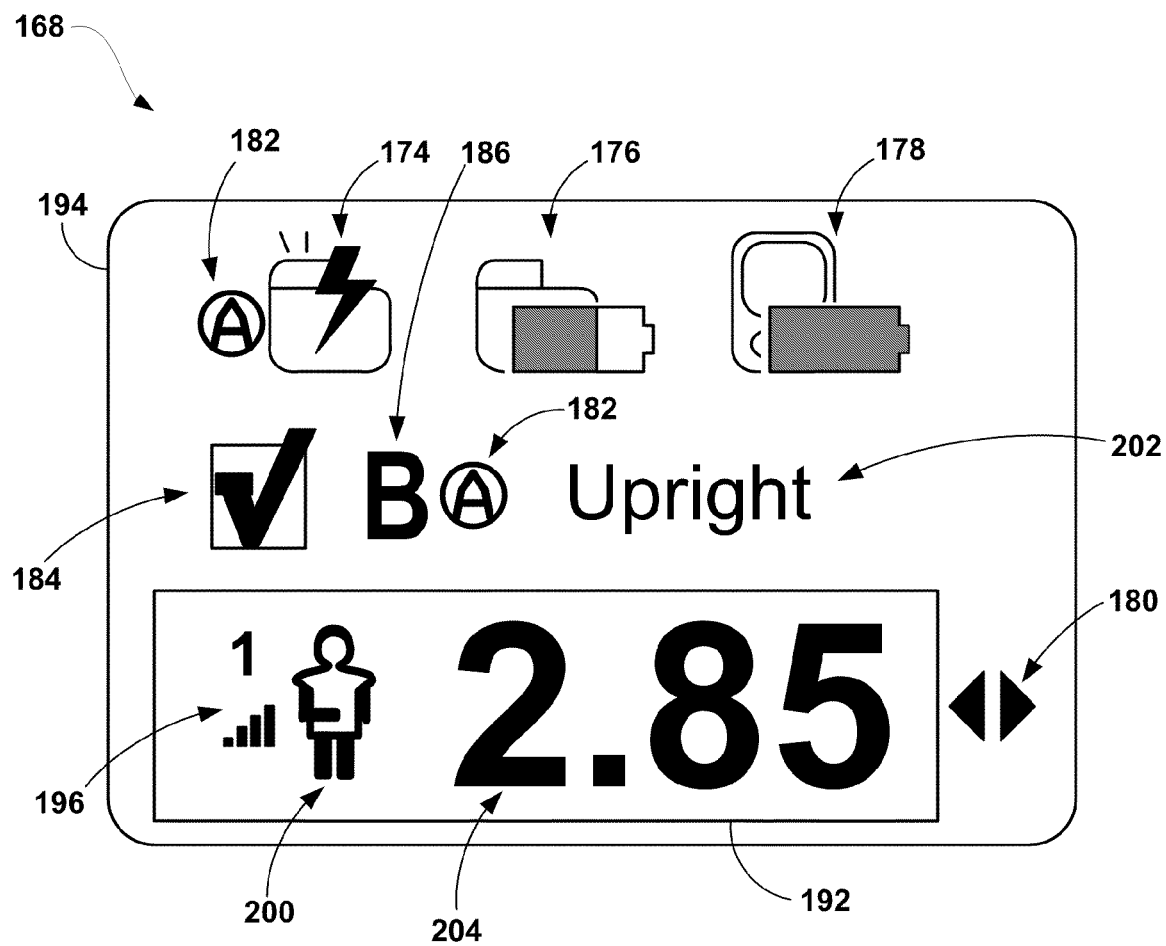
FIG. 10 is a conceptual diagram illustrating an example user interface of a patient programmer for delivering therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or the patient.

Group identifier 186 indicates that group "B" is active, and automatic posture response icon 182 indicates group "B" (containing one or more programs) is activated to allow IMD 14 to automatically adjust therapy according to the patient 12 posture state. In the example shown in FIG. 10, user interface 168 indicates the posture state determined by IMD 14, e.g., via posture state indication 200 and supplementary posture state indication 202. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40.

In addition, posture state indication 200 shows that IMD 14 is detecting that patient 12 is in the upright or standing posture based on the output of posture state module 86 (FIG. 4A). Supplementary posture state indication 202 supplements posture state indication 200 by explaining in words to patient 12 the exact posture being detected by posture state module 86 of IMD 14. Posture state indication 200 and supplementary posture state indication 202 presented via user interface 168 change according to the sensed, or detected, posture state detected by IMD 14. The posture state may be communicated to the external programmer immediately after IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 view other programs within group "B" using selection arrows 180. Selection box 192 may be moved to select other screen levels with control pad 40 (FIG. 2) of patient programmer 30 in order to navigate through other stimulation groups or adjustable elements of the therapy. When patient 12 selects a different program with control pad 40, program identifier 196 is updated to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, a somatosensory indication, such as a different numbers of vibratory pulses delivered in sequence or vibratory pulses of different lengths, amplitudes, or frequencies.

As previously described, examples of the present disclosure relate to systems and techniques for generating baseline patient information based on patient data corresponding to one or more periods of time in which the patient is not receiving posture-responsive therapy. The patient data may include one or more of posture state data indicative of a plurality of patient posture states during the respective period of time and therapy adjustment data indicative of therapy adjustments made by patient 12 during the respective time period. The generated baseline patient information may be compared posture-responsive patient information, i.e., patient information generated based on patient data corresponding to one or more time period in which posture-responsive therapy is delivered to the patient from a medical device. In some examples, the comparison of baseline and posture-responsive patient information may allow a medical device, such as IMD 14, or a user, such as a clinician and/or patient, to evaluate the efficacy of posture-responsive therapy delivered to the patient.

Figure 11:
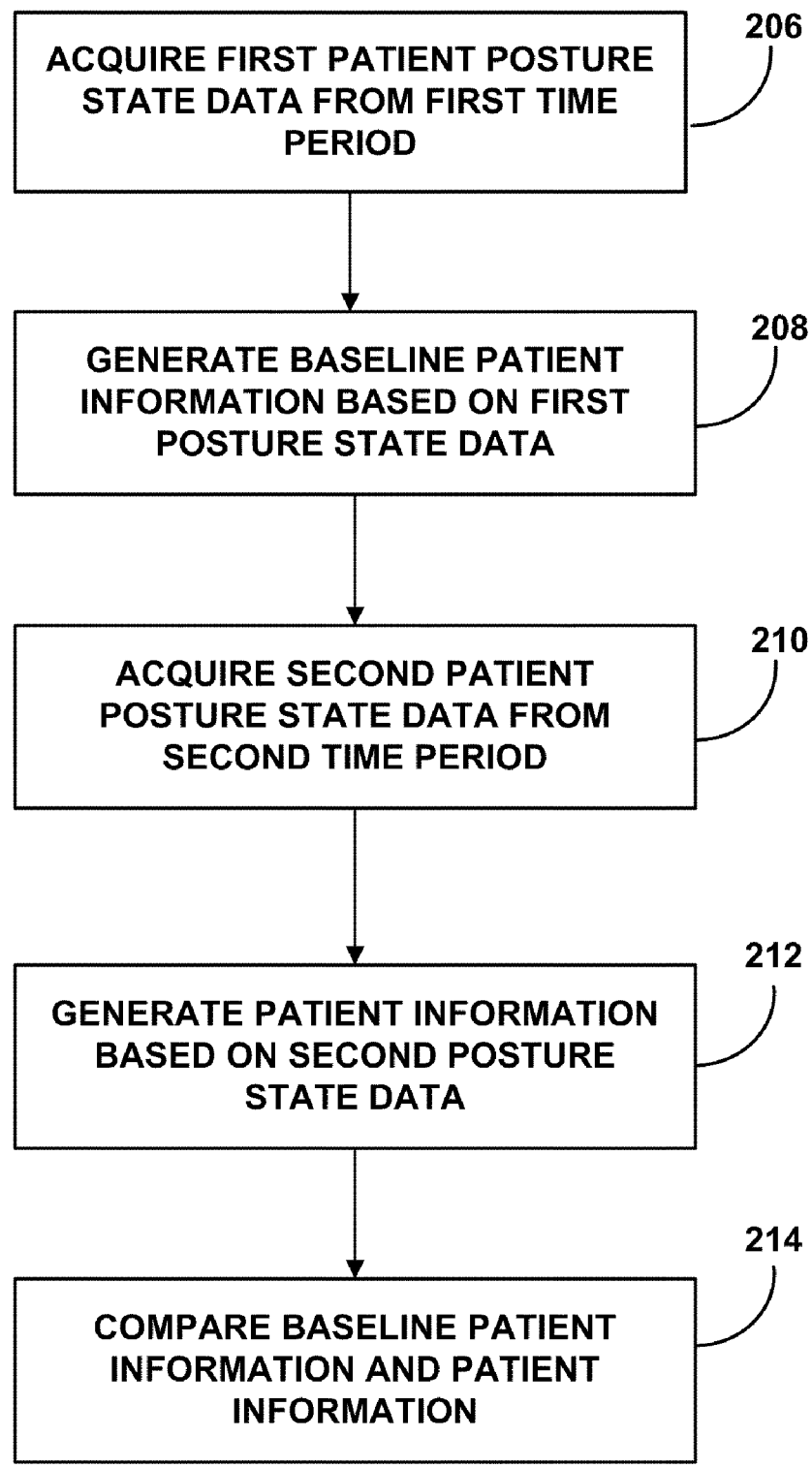
FIG. 11 is a flow diagram illustrating an example technique for generating baseline and posture-responsive patient information.

FIG. 11 is a flow diagram illustrating an example technique for generating baseline and posture-responsive patient information. For purposes of illustration, the example technique is described with respect to system 10 of FIG. 1A although such a technique may be utilized by any suitable medical system or device configured to delivery therapy to a patient according to the detected patient posture state. Moreover, while the example technique of FIG. 11 is described with respect to external programmer 20, examples are not limited as such. For example, programmer 30, programmer 60 or any other suitable device may be used to perform all or a portion of the example of FIG. 11. In some aspects, the patient data in the example of FIG. 11 is described with respect to posture state data indicative of the posture states of patient 12 during a first and second time period. However, in some examples, the patient data may additionally or alternatively include therapy adjustment information indicative of therapy adjustment made by patient 12 during the first and second time periods.

In the example of FIG. 11, programmer 20 acquires first posture state data indicative of the posture state of patient 12 during a first time period in which patient 12 did not receive posture-responsive therapy from IMD 14 (206). In general, the first time period may correspond to a period of time in which IMD 14 is not delivering stimulation therapy to patient 12 according to the posture state of patient 12. For example, during the first time period, IMD 14 may not deliver any type of stimulation to patient 12 or IMD 14 may deliver stimulation therapy but not according to the posture state of patient 12 detected via posture state module 86.

In some examples, programmer 20 may acquire the first posture state data from external sensor 15. As described above, in some examples, external sensing device 15 may monitor the posture state of patient 12 via posture state module 87 during a first time period when IMD 14 is not delivering posture-responsive therapy to patient 12. External sensing device 15 may store the posture state data 85 generated from posture state module 87 while monitoring the posture state of patient 12 in memory 85. Programmer 20 may retrieve the stored posture state data 85 from external sensing device 15 using telemetry circuitry 93, 110.

Alternatively or additionally, programmer 20 may acquire the first posture state data from IMD 14. As described above, in some examples, IMD 14 may monitor the posture state of patient 12 via posture state module 86 during a first time period when IMD 14 is not delivering posture-responsive therapy to patient 12. While monitoring the posture state of patient 12, IMD 14 may be implanted within patient 12 or may be located external to patient 12, e.g., functioning as an external trial stimulation device. Similar to that of external sensing device 15, IMD 14 may store the patient data 83 generated from posture state module 86 while monitoring the posture state of patient 12 in memory 82. To acquire the posture state data, programmer 20 may retrieve the stored patient data 83 from IMD 14 using telemetry circuitry 88, 110.

Programmer 20 may periodically acquire the stored posture state data from IMD 14 and/or external sensing device 15 during the first time period, or may acquire the stored posture state data after the first time period has ended. Upon acquiring the first posture state data, programmer 20 may store the first posture state data acquired from IMD 14 and/or external sensing device 15 in memory 108 for subsequent analysis.

Using all or a portion of the first posture state data acquired from IMD 14 and/or external sensing device 15, processor 104 (FIG. 6) of programmer 20 may generate baseline patient information (208). In some examples, the baseline patient information includes one or more of baseline posture state information or baseline therapy adjustment information. Baseline postures state information may include baseline proportional posture state information, baseline sleep quality information, or baseline posture state adjustment information. Baseline therapy information may include the number of therapy adjustments received over all or a portion of the first time period. Since the baseline patient information in FIG. 11 is generated based on the first posture state data, the baseline patient information provides reference posture state information representative of the behavior and habits of patient 12 in terms of posture state during a period of time in which patient 12 is not receiving posture-responsive therapy from IMD 14. Accordingly, the generated baseline patient information may facilitate the evaluation of the efficacy of posture responsive therapy by providing a baseline with which posture-responsive patient information may be compared.

To generate posture-responsive patient information, programmer 20 may acquire second posture state data, which is indicative of the postures state of patient 12 during a second time period in which IMD 14 delivers posture-responsive therapy to patient 12 (210). In particular, during the second time period, IMD 14 may detect the posture state of patient 12 and deliver stimulation therapy to patient 12 according to the detected posture state.

Programmer 20 may acquire the second posture state data from IMD 14 or external sensing device 15 in a manner the same or similar to that described with respect to the acquisition of first posture state data. In some examples, programmer 20 may acquire the second posture state data from IMD 14 since IMD 14 is monitoring the posture state of patient 12 in conjunction with the delivery of posture-responsive therapy to patient 12. IMD 14 may store the posture state data from posture state module 86 in memory 82. All or a portion of the posture state data may be retrieved from IMD 14 by programmer 20 using telemetry circuits 88, 110. Additionally or alternatively, programmer 20 may acquire the second postures state data from external sensing device 15, which may also be monitoring the patient posture state during the time period that IMD 14 is delivering posture-responsive therapy from IMD 14. External sensing device may store the posture state data from posture state module 87 in memory 85. All or a portion of the posture state data may be retrieved from external sensing device 15 by programmer 20 using telemetry circuits 93, 110.

In some examples, programmer 20 acquires the second posture state data from the same device that the first posture state data was acquired. For example, if programmer 20 acquired the first posture state data from external sensor 15, then programmer 20 may also acquire the second posture state data from external sensor 15. As another example, if programmer 20 acquired the first posture state data from IMD 14, then programmer 20 may also acquire the second posture state data from IMD 14. In this manner, the first and second posture state data may be consistent with one another at least to the extent that the respective data was generated by the same posture sensors and posture state module, e.g., posture state module 86 or posture state module 87. However, in other examples, IMD 14 may acquire the first and second posture state data from different devices. For example, IMD 14 may acquire the first posture state date from external sensing device 15 and second posture state data from IMD 14, especially in cases in which IMD 14 was not operating to monitor the posture state of patient 12 during all or a portion of the first time period. In still other examples, programmer 20 may acquire the first and/or second posture state data from multiple devices, e.g., from both IMD 14 and external sensing device 15. However, programmer 20 may not use all the acquired posture state data in generating the baseline and/or posture-responsive patient information.

In general, the first and second posture state data acquired by programmer 20 is data indicative of the posture state of patient 12 during the first and second time periods, respectively. For example, in some cases, the posture state data may include specific information as to the posture states of patient 12 throughout the first time period as detected by posture state module 86 of IMD 14 and/or posture state module 87 of external sensing device 15. For example, posture state module 86 may receive one or more posture sensor signals from posture sensor(s) on or within patient 12 and detect patient posture state based on the received sensor signal(s), e.g., using one or more posture detection techniques described with regard to FIGS. 8A-8C. The particular posture states detected by posture state module 86 may then be stored as patient data 83 within memory 82 and subsequently acquired by programmer 20. In other examples, the posture state data acquired by programmer 20 from IMD 14 and/or external sensing device 15 may include information regarding the one or more posture sensor signals, e.g., raw sensor signal data, received by posture state modules 86 or 87 without a particular posture state determination. In such a case, programmer 20 may acquire posture state data including the posture sensor signal data, and processor 104 of programmer 20 may then determine the one or more posture states of patient 12 which corresponds to the acquired sensor signal data, e.g., using one or more posture detection techniques described with regard to FIGS. 8A-8C.

Referring still to FIG. 11, processor 104 (FIG. 6) of programmer 20 may generate posture-responsive patient information based on the second posture state data acquired from IMD 14 and/or external sensing device 15 (212). For purposes of comparison, the posture-responsive patient information may be consistent with that of the baseline patient information. For example, if the baseline patient information generated based on the first posture state data includes baseline posture state information, such as, baseline sleep quality information, then processor 104 may generate posture-responsive sleep quality information based on the second patient data.

Patient information, whether it be baseline or posture-responsive, may include posture state information. Posture state information may objectify one or more aspects of a patient's posture state during the respective time period. For example, the baseline posture state information may include, but is not limited to, the number of posture state transitions a patient has undertaken during the first period of time, the relative amount of time a patient has occupied one or more posture states during the first period of time, the number of posture state transitions that a patient has undertaken while in a general lying posture states, and the like.

By objectifying the patient's posture state during one or more time periods using posture state data, the posture state information may be representative of the patient's posture state behavior during all or portions of the one or more time periods during which the patient's posture state was monitored. Such patient information may facilitate the evaluation of a patient's movement during one or more time periods in a manner beyond that of evaluation based on a patient's subjective input of his/her posture state during the one or more time periods. In particular, baseline posture state information that is generated based on posture state date indicative of a patient's posture state over a period of time that the patient is not receiving posture-responsive therapy may be representative of the patients posture state behavior when the patient is not receiving posture-responsive therapy. Likewise, posture-responsive posture state information that is generated based on posture state data indicative of a patient's posture state over a period of time that the patient is receiving posture-responsive therapy may be representative of the patient's posture state behavior when the patient is receiving posture-responsive therapy.

In some examples, posture state information generated by programmer 20 or any other suitable device includes proportional posture state information. Proportional posture state information generated from posture state data from any given period of time may illustrate the relative amount of time that a patient occupied each of one or more posture states over that time period. Accordingly, baseline proportional posture information generally illustrates the relative amount of time that a patient occupied each of one or more postures states during a time period in which the patient is not receiving posture-responsive therapy. In the example of FIG. 11, processor 104 of external programmer 30 may analyze the acquired first posture state data to generate baseline proportional posture information for patient 12 for one or more portions of the first time period. Likewise, posture-responsive proportional posture information generally illustrates the relative amount of time that a patient occupied each of one or more postures states during a time period in which the patient is receiving posture-responsive therapy. In the example of FIG. 11, processor 30 may analyze the acquired second posture state data to generate posture-responsive proportional postures state information for patient 12 for one or more portions of the second time period.

In some examples, posture state information includes sleep quality information. Sleep quality information generated by programmer 20 or other suitable device from posture state data may include the number of times a patient has transitioned between lying down postures in a given time period or the number of times a patient transitioned from each posture state. Accordingly, baseline sleep quality information may generally correspond to the number of times a patient has transitioned between lying down postures or the number of times a patient transitioned from each posture state during a time period in which the patient is not receiving posture-responsive therapy. In the example of FIG. 11, processor 104 of external programmer 30 may analyze the acquired first posture state data to generate baseline sleep quality information for patient 12 for one or more portions of the first time period. Likewise, posture-responsive sleep quality information may generally correspond to the number of times a patient has transitioned between lying down postures or the number of times a patient transitioned from each posture state during a time period in which the patient is receiving posture-responsive therapy. In the example of FIG. 11, processor 30 may analyze the acquired second posture state data to generate posture-responsive sleep quality information for patient 12 for one or more portions of the second time period.

In some examples, the posture state information may include posture state adjustment information. Posture state adjustment information generated by programmer 20 or other suitable device from posture state data may include the number of posture state adjustments made during one or more time intervals during a particular time period. Accordingly, baseline posture state adjustment information may generally represent the number of posture state adjustments that a patient has made during a time period in which the patient is not receiving posture-responsive therapy. In the example of FIG. 11, processor 104 of external programmer 30 may analyze the acquired first posture state data to generate baseline posture state adjustment information for patient 12 for one or more portions of the first time period. Likewise, posture-responsive posture state adjustment information may generally represent the number of posture state adjustments that a patient has made during a time period in which the patient is receiving posture-responsive therapy. In the example of FIG. 11, processor 30 may analyze the acquired second posture state data to generate posture-responsive posture state adjustment information for patient 12 for one or more portions of the second time period.

Additionally or alternatively, patient information, whether it be baseline or posture-responsive, may include therapy adjustment information. Therapy adjustment information may be generated based on therapy adjustment data indicative of therapy adjustments made by patient 12. A patient therapy adjustment may be made by a patient by selecting or adjusting one or more parameter values for a current program, e.g., via a patient programmer. For example, an adjustment may be made to one or more of an amplitude, a pulse width, a pulse rate, an electrode combination, or an electrode polarity. In addition, a therapy adjustment may be entered by patient 12 simply selecting a different therapy program to determine the stimulation therapy that is applied. In response to a patient therapy adjustment, IMD 14 may apply the patient therapy adjustment to therapy that is delivered to the patient 12. However, IMD 14 may apply the patient therapy adjustment on a temporary basis while patient 12 resides in the posture state. The next time that patient 12 occupies the posture state, IMD 14 may again apply the existing therapy parameters for the posture state according to the established posture state-responsive therapy programming. In this case, patient 12 may again enter patient therapy adjustments, if desired or necessary to achieve better efficacy.

The therapy adjustments may be made by patient 12 to modify one or more parameters of therapy delivered in a posture state-responsive therapy mode in order to enhance efficacy. An analysis of the number of therapy adjustments by a clinician may provide objectification information about the efficacy of the posture state-responsive therapy delivered to patient 12. Furthermore, an analysis of the number of therapy adjustment made during a time period during which posture-responsive therapy was delivered compared to that of the number of therapy adjustments made during time period that posture-responsive therapy was delivered may provide objective information about the efficacy of posture-responsive therapy, at least to the extent that the posture-responsive therapy influence the amount of therapy adjustments required of a patient. For example, an increase in the number of patient adjustments to therapy parameters during posture-responsive may indicate that the level of therapeutic efficacy provided by the posture-responsive therapy is insufficient, in addition to increasing the amount of therapy adjustments required by patient 12. A reduction in the number of adjustments made by a user during posture-responsive therapy compared to that of a baseline period made provide an objective indication that the posture-responsive therapy may be successful since the therapy delivered to patient 12 during posture-responsive therapy required less patient therapy adjustments.

Examples of objective information that may be used as patient information may include one or more examples described in co-pending U.S. patent application Ser. to Skelton et al., filed on the same date as the present application and entitled "DATA ANALYSIS FOR POSTURE RESPONSIVE THERAPY" Ser. No. 12/433,632 and co-pending U.S. Provisional Patent Application Ser. No. 61/080,000, to Skelton, et al., filed Jul. 11, 2008, titled "DATA ANALYSIS FOR POSTURE RESPONSIVE THERAPY". The entire content of each of these applications is incorporated herein by reference.

In any case, in the example of FIG. 11, once programmer 20 has generated both baseline patient information and posture-responsive patient information, external programmer 20 compares the generated baseline patient information to the posture-responsive patient information (214). The comparison of the baseline patient information to the posture-responsive patient information may facilitate the evaluation of the efficacy of posture-responsive therapy by illustrating the differences, if any, between the posture state behavior of a patient when they are receiving posture-responsive therapy and when they are not receiving posture-responsive therapy.

The differences between the baseline patient information and posture-responsive patient information may be attributed to the delivery of posture-responsive therapy, thereby facilitating the evaluation of the posture-responsive therapy. For example, if a statistically significant difference is determined to exist between the respective patient information, the posture-responsive therapy may be considered relatively effective, at least to the extent that the observed change in posture state behavior is considered an improvement. Conversely, if substantially no difference is determined to exist between the respective patient information or the difference is relatively minimal, the posture-responsive therapy may be considered relatively ineffective, or effective at least to the extent that posture-responsive therapy reduces the amount of programming, e.g., manual therapy adjustments, that patient 12 must perform.

Figure 13:
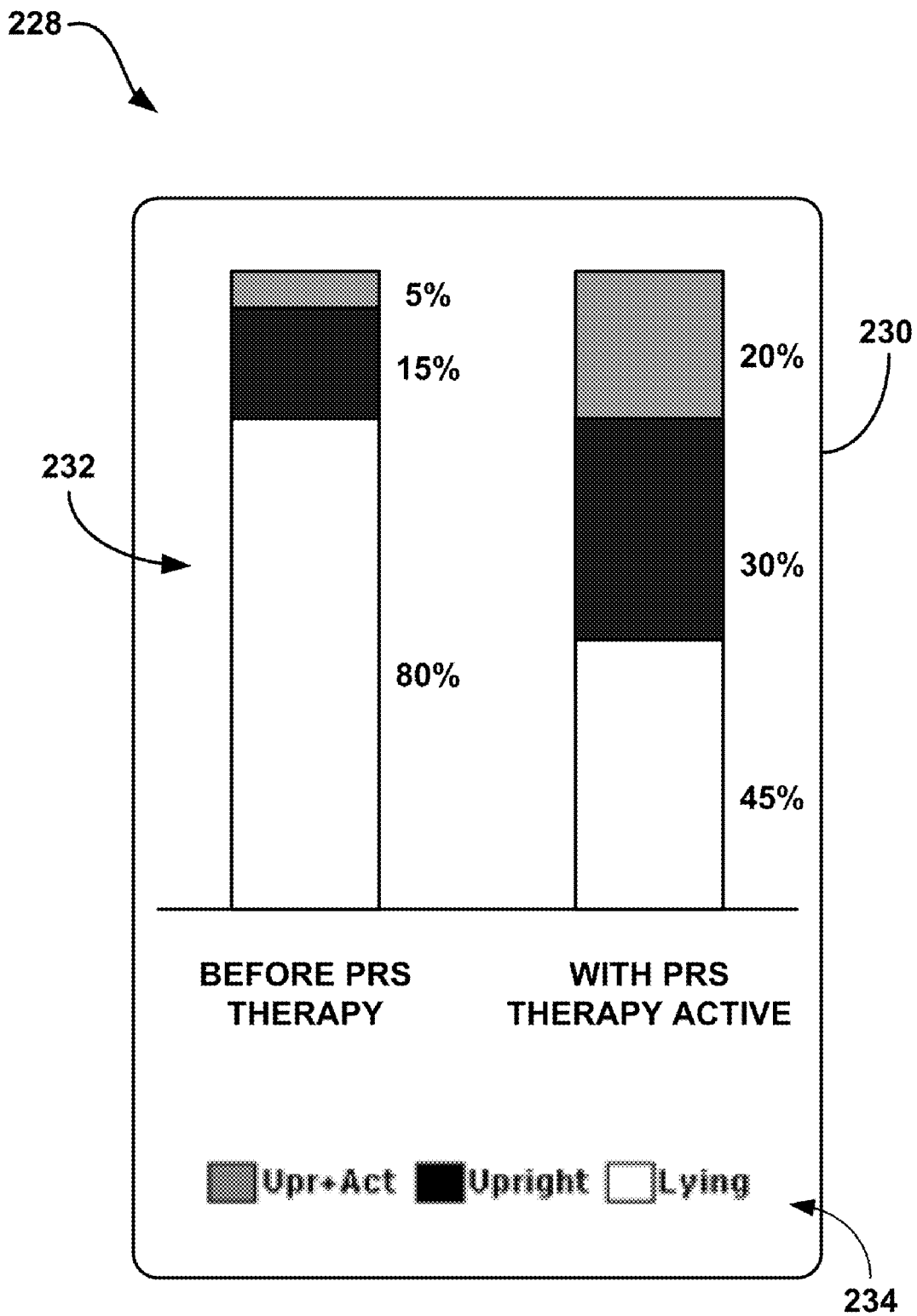
FIG. 13 is a conceptual diagram illustrating an example user interface presenting a comparison of baseline proportional posture information to posture-responsive proportional posture information.

In some examples, external programmer 20 may compare the baseline patient information to posture-responsive patient information by presenting some or all aspects of the baseline and posture-responsive patient information to a user via user interface 106 (FIG. 6). User interface 106 may present both the baseline and posture-responsive patient information using any suitable graphical or numerical form. For example, baseline and posture-responsive proportional posture information may each be presented in graphs showing the percentage of time patient 12 engaged in each posture state over the baseline and posture-responsive time periods, based on the posture state data acquired from IMD 14 and/or external sensing device 15. FIG. 13 illustrates one example of the presentation of baseline proportional posture state information and posture-responsive proportional posture state information by external programmer 20 to compare the baseline and posture-responsive proportional posture state information generated from posture state data acquired form IMD 14 and/or external sensing device 15.

In some examples, rather than simply presenting baseline patient information and posture-responsive patient information to user via user interface 106, processor 104 may analyze the baseline with respect to the posture-responsive patient information to quantify one or more differences between the baseline and posture-responsive patient information. For examples, processor 106 may determine an overall percent difference between a posture state variable, such as patient posture adjustments or patient therapy adjustments, by comparing the baseline and posture-responsive patient information. Such information may then be presented to a user via user interface 106. Processor 106 may apply any suitable statistical techniques to compare the baseline and posture-responsive patient information in a manner that facilitates evaluation of the posture-responsive therapy, e.g., by determining one or more differences between the baseline and posture-responsive patient information.

Based on the comparison of the baseline and posture-responsive postures state information, one or more aspects of posture-responsive therapy may be adjusted. In some examples, by presenting both the baseline and posture-responsive patient information (or the difference between the respective patient information) to a user such as a clinician or patient, the user may determine that it is desirable to adjust one or more stimulation therapy parameters and implement the desired adjustment by communicating with IMD 14 via external programmer 20. For example, based on the comparison of the baseline patient information and posture-responsive patient information, a user may indicate to programmer 20 that posture-responsive therapy should be turned off. Programmer 20 may then generate and send an indication consistent with the user input to IMD 14, which may then turn off the posture-responsive aspect of the therapy delivered to patient 12. A similar approach may be used by a user to adjust one or more stimulation parameter values or even one or more aspects of the posture state detection technique used by posture state module 86 to detect the posture state of patient 12.

Alternatively or additionally, IMD 14 or programmer 20 may be configured to automatically or semi-automatically (e.g., with user confirmation) adjust one or more aspects of the therapy delivered by IMD 14 to patient 12 based on the comparison of the baseline patient information to the posture-responsive patient information. For example, processor 80 of IMD 14 or processor 105 of programmer 20 may analyzed the generated baseline and posture-responsive patient information to determine one or more difference between the patient information. Based on the differences, if any, between the baseline and posture-responsive patient information, one or more aspects of therapy may be automatically or semi-automatically adjusted. For example, if the comparison of baseline and posture-responsive patient information indicates no difference between a patient's posture state or therapy adjustment behavior when posture-responsive therapy is and is not delivered, then processor 80 of IMD 14 may adjust one or more therapy parameters, such as stimulation amplitude, or may modify the posture detection technique used by posture state module 86 to detect patient posture state in a manner designed to elicit some change in the patient's posture state or therapy adjustment behavior.

As another example, if processor 80 determines that the difference between the baseline and posture-responsive patient information are indicative of an undesirable change in the patient's posture state behavior during delivery of posture-responsive therapy (e.g., the number of posture state adjustment made by a patient has drastically decreased since posture-responsive therapy has been delivered or patient therapy adjustments have increased), processor 80 may automatically turn-off the posture-responsive aspect of the therapy deliver to patient 12 via IMD 14. Conversely, processor 80 may turn posture responsive stimulation therapy back on, e.g., if baseline patient information generated from patient data from a time period after the posture-responsive therapy has been turned off indicates that a patient's posture state or therapy adjustment behavior has undesirably changed since posture-responsive therapy has been turned off. In some cases, processor 104 of external programmer 20 may compare and analyzed the patient information as described, and then communicate with IMD 14 to implement the one or more desired adjustments. In any case, system 10 may generate baseline patient information and automatically or semi-automatically adjust one or more aspects of therapy delivered to patient 12 by IMD 14 based on a comparison of the baseline patient information to posture-responsive patient information.

Programmer 20 may store one or more of the acquired patient data, generated baseline and posture-responsive patient information, and information associated with the comparison of the baseline patient information and posture-responsive patient information within memory 108. In this manner, processor 104 may access the information stored in memory 108 at later time, e.g., based on input received from a user indicating that the user would like programmer 20 to present a comparison of the stored baseline and posture-responsive patient information in one form or another. In some examples, processor 104 may access the stored patient data and/or patient information to update patient data and/or information based on new patient data acquired form IMD 14 or external sensing device 15.

Although in the example technique of FIG. 11 programmer 20 acquires the patient data from IMD 14 and/or external sensing 15, and then generates baseline and posture-responsive patient information based on the acquired patient data, examples are not limited to such a configuration. For example, in some examples, rather than external programmer 20 acquiring patient data and generating patient information, processor 80 of IMD 14 (FIG. 4A) and/or processor 81 of external sensing device 15 (FIG. 4B) may acquire patient data, e.g., from memory 82 and memory 85, respectively, and also generate baseline and/or posture-responsive patient information based on the acquired patient data. In such a case, IMD 14 and/or external sensing device 15 may send the generated baseline and posture-responsive patient information to external programmer 20, such as, patient programmer 30 (FIG. 2) or clinician programmer 60 (FIG. 3), for comparison of the generated baseline patient information to the posture-responsive information. For example, external programmer 20 may present the generated baseline and posture-responsive patient information to a user so that the user may evaluate the efficacy of the posture-responsive therapy. Alternatively or additionally, processor 80 (FIG. 4A) and/or processor 81 (FIG. 4B) may compare the baseline and posture-responsive patient information, and store the comparison information in memory 82 and 85, respectively. In some examples, the comparison information may then be sent to external programmer 20, e.g., for presentation to a user. Furthermore, as described above, in some examples, processor 80 of IMD 14 may analyze the comparison information and automatically or semi-automatically adjustment one or more aspects of the stimulation therapy delivered by IMD 14 to patient 12.

Figure 12:
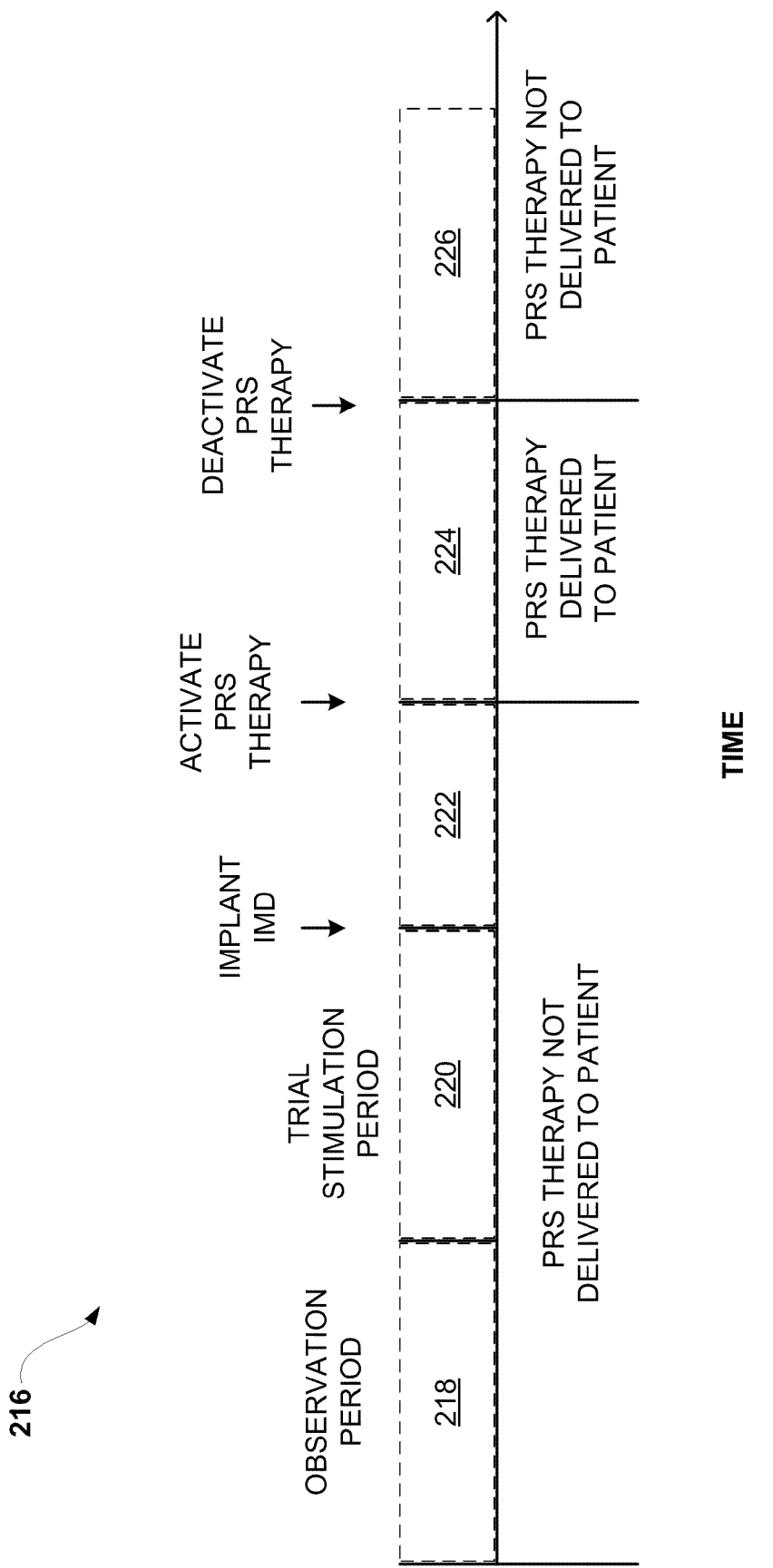
FIG. 12 is a plot illustrating an example timeline including multiple time periods during which patient posture state and/or therapy adjustments may be monitored to generate patient information.

FIG. 12 is a plot illustrating an example timeline 216 including multiple time periods 218, 220, 222, 224, 226 during which the posture state and/or therapy adjustments of patient 12 may be monitored to generate patient information. As will apparent from the following description, during time periods 218, 220, 222, 226, patient 12 does not receive posture-responsive therapy. Accordingly, the posture state and/or therapy adjustments of patient 12 may be monitored during all or portions of time periods 218, 220, 222, 226, and the resulting patient data may be used to generate baseline patient information. Conversely, during time period 224, patient 12 receives posture responsive therapy from IMD 14. Accordingly, the posture state and/or therapy adjustments of patient 12 may be monitored during all or portions of time period 224, and the resulting patient data may be used to generate posture-responsive patient information. The example of FIG. 12 is described with reference to external programmer 20 generating baseline and posture-responsive patient information. However, other configurations are contemplated, including one or more of IMD 14, programmer 30, and programmer 60 generating patient information.

Time period 218 corresponds to a period of time during which only an external sensing device, such as, external sensing device 15, monitors the posture state of patient 12. As previously described, external sensing device 15 is not capable of delivering stimulation therapy to patient 12, much less posture-responsive therapy. As such, patient 12 generally will not make therapy adjustments during time period 218. Instead, time period 218 may be an observational period during which the posture state behavior is observed, e.g., for diagnostic purposes, by external sensing device 15. Accordingly, during time period 218, patient 12 does not receive posture-responsive therapy, and the patient data from external sensing device 15 during time period 218 may be used by programmer 20 to generate baseline posture state information.

After time period 218, patient 12 may receive temporary or trial stimulation therapy from an external trial stimulation device, e.g., via percutaneously implanted stimulation leads during time period 220. The trial stimulation may be delivered to patient 12 during time period 220 to determine whether chronic stimulation therapy may be beneficial to patient 12 before undergoing the procedure to implant a medical device, such as IMD 14. Notably, the trial stimulation provided to patient 12 during time period 220 is delivered on a non-posture-responsive basis. Accordingly, during time period 220, external sensing device 15 may monitor the posture state and/or therapy adjustments of patient 12. Additionally or alternatively, the external trial stimulation device may include components necessary to monitor the posture state and/or therapy adjustments of patient 12 during time period 220. All or a portion of the patient data gathered by external sensing device 15 and/or the external stimulation device during time period 220 may be used by programmer 20 to generate baseline patient information.

After time period 220, IMD 14 may be implanted in patient 12. Once IMD 14 is successfully implanted in patient 12, IMD 14 may begin delivering stimulation therapy to patient 12 albeit on a non-posture-responsive basis. For example, the therapy delivered to patient 12 from IMD 14 may be substantially similar to that of delivered to patient 12 from the external trial stimulator during time period 220. In other examples, while IMD 14 has been implanted, the delivery of stimulation to patient 12 may be turned off during all or a portion of time period 222. Accordingly, during time period 220, IMD 14 may monitor the posture state and/or therapy adjustments of patient 12 via posture state module 86. Additionally or alternatively, external sensing device 15 may monitor the posture state and/or therapy adjustments of patient 12. All or a portion of the patient data gathered by external sensing device 15 and/or IMD 14 during time period 222 may be used by programmer 20 to generate baseline patient information.

At the beginning of time period 224, IMD 14 is activated to deliver posture-responsive therapy to patient 12. For example, throughout time period 224, IMD 14 may detect the posture state of patient 12 via posture state module 86 (FIG. 4A) and adjust one or more aspects of therapy according to the detected posture state of patient 12. Accordingly, during time period 224, IMD 14 may monitor the posture state and/or therapy adjustments of patient 12 via posture state module 86. Additionally or alternatively, external sensing device 15 may monitor the posture state and/or therapy adjustments of patient 12 during time period 224. All or a portion of the patient data gathered by external sensing device 15 and/or IMD 14 during time period 224 may then be used by programmer 20 to generate posture-responsive patient information. As previously described, the posture-responsive patient information may be compared to baseline patient information.

Time period 224 ends and time period 226 begins when the posture-response mode of IMD 14 is deactivated. From that time on, during time period 226, IMD 14 may continue to delivery stimulation therapy to patient although IMD 14 does not deliver the therapy on a posture-responsive basis. Alternatively, IMD 14 may not delivery stimulation therapy of any sort to patient 12 during time period 226. Accordingly, during time period 226, IMD 14 may monitor the posture state and/or therapy adjustments of patient 12 via posture state module 86. Additionally or alternatively, external sensing device 15 may monitor the posture state and/or therapy adjustments of patient 12 during time period 226. All or a portion of the patient data gathered by external sensing device 15 and/or IMD 14 during time period 226 may then be used by programmer 20 to generate baseline patient information.

Overall, one or both of the posture state data indicative of the posture state of patient 12 during time periods 218, 220, 222, 226 and therapy adjustment data indicative of patient therapy adjustments during time period 218, 220, 222, 226 may be used by programmer 20 to generate baseline patient information. In some examples, programmer 20 generates baseline patient information based on patient data from all or a portion of only one of time periods 218, 220, 222, 226. In other examples, programmer 20 generates baseline patient information based on a combination of patient data from all or a portion of two or more of time periods 218, 220, 222, 226. In some examples, programmer 20 may generate separate baseline patient information for each of time periods 218, 220, 222, 226 based on patient data from the corresponding time period. The overall length of the baseline time period may be any appropriate length, and may be on the order of hours, days, and months, for example. In some examples, the baseline time period may be approximately 1 days to approximately 1 year, such as, e.g., approximately 1 day to approximately 1 month or approximately 1 day to approximately 1 week.

In some examples, programmer 20 may generate baseline patient information based on patient data corresponding to time period 226 separately from that of baseline patient information based on patient data corresponding to one or more of time period 218, 220, 222. While posture-responsive therapy was not delivered to patient 12 during each of time periods 218, 220, 222, 226, time period 226 corresponds to a time period after IMD 14 has delivered posture-responsive therapy unlike time periods 218, 220, 222 which all occur prior to IMD 14 delivering posture-responsive therapy to patient 12.

Accordingly, the two respective types of baseline patient information may facilitate the evaluation of posture-responsive therapy from two different perspectives. For examples, while both types of baseline patient information may be generally used to illustrate differences in the posture state and therapy adjustment behavior of patient 12 with posture-responsive therapy active compared to inactive, baseline patient information generated from patient data from all or a portion of time period 226 may be compared to posture-responsive patient information to illustrate the residual effect that posture-responsive therapy has a patient's posture state and therapy adjustment behavior. For examples, a user such a clinician may be able to compare posture-responsive patient information to baseline patient information from time period 226 on a dynamic basis to gauge the relative amount of time that a patient experiences the affects of posture-responsive therapy in one form or another after the posture-responsive therapy has been deactivated.

As previously described with regard to FIGS. 8A-8C, a variety of techniques may used by posture state module 86 of IMD 14 during posture-responsive therapy to detect the posture state of patient 12 based on sensed posture sensor signals. In some cases, prior to the implantation of IMD 14 and detection of patient posture state via posture state module 86, the posture detection technique used to deliver posture-therapy to patient 12 may be undecided. Accordingly, it may be desirable for the posture state of patient 12 prior to time period 224 (e.g., during one or more of time periods 218, 220, 222) to be monitored in a manner to account for this unknown variable.

For purposes of illustration, a scenario may be imagined in which posture state sensor signal may be processed by posture state module 86 of IMD 14 according to a first posture detection algorithm or a second posture detection algorithm to detect the posture state of patient 12. However, it may be unknown which of the first or second posture detection algorithms most accurately detect the posture state of patient 12 until IMD 14 is implanted in patient 12 and the posture state module 86 is actively detecting the posture state of patient 12. Additionally, in some cases, although posture state module 86 may begin detecting the posture state of patient 12 using the first algorithm, at some later time, an adjustment may be made such that posture state module 86 detect the patient posture state using the second posture detection algorithm.

Therefore, to provide posture state data for time periods 218, 220, 222 that is consistent with the posture state data from IMD 14 during time period 224, external sensing device 15 and/or IMD 14 may store posture state data for patient 12 using both the first and second detection algorithms to detect the posture state of patient 12 via posture state module 87. Then, once it is determined which posture detection algorithm that IMD 14 will use to deliver posture-responsive therapy to patient 12 during time period 224, processor 104 of programmer 20 may acquire the posture state data corresponding to the selected detection algorithm from external sensing device 15 and/or IMD 14, and generate baseline posture state information based on that posture state data.

Alternatively or additionally, external sensing device 15 and/or IMD 14 may store sensor signal information from time periods 218, 220, 222, in memory 85, 82. In such an example, once it is determined which posture detection algorithm that IMD 14 will use to deliver posture-responsive therapy to patient 12 during time period 224, the stored sensor signals may be analyzed, e.g., by one or more of processors 80, 81, 104, using the selected posture state detection algorithm. Posture state information may then be generated based on posture state data indicative of the posture states of patient 12 detected using the same posture detection algorithm used by IMD 14 to deliver posture-responsive therapy. In either case, such a process may allow the baseline posture state information and posture-responsive posture state information may be consistent with each other, at least to the extent that the same posture state detection algorithm was used to detect patient posture state regardless of the time period the posture state was monitored by system 10.

FIG. 13 is a conceptual diagram illustrating an example user interface 228 for presenting a comparison of baseline proportional posture information to posture-responsive proportional posture information. User interface 228 is described as being displayed by external programmer 20. However, user interface 228 may also be displayed by patient programmer 30, clinician programmer 60, or some other external device. In any case, user interface 228 displays baseline and posture-responsive patient information generated based on posture state data indicative of the posture state of patient 12 during time periods when posture-responsive therapy is and is not, respectively, delivered by IMD 14 to patient 12.

In the example of FIG. 13, screen 230 of user interface 228 presents patient information graph 232 and posture state key 234. Patient information graph 232 displays both baseline proportional posture state information and posture-responsive proportional posture state information consistent with that generated by processor 104 (FIG. 6) based on posture state data acquired from IMD 14 and/or external sensing device 15. Patient information graph 232 includes the percentage of time, or posture durations, for each of the baseline patient information and posture-responsive patient information.

In the example of FIG. 13, patient information graph 232 indicates the percentage of time during which the patient occupied each of three posture states during a time period before posture-responsive stimulation (PRS) therapy was active and during a time period with PRS therapy active. In particular, each bar in the bar graph corresponds to one of the time intervals, and each bar includes multiple bar segments, where each segment indicates the proportional amount of time the patient occupied a particular posture state in relation to the overall amount of time of the baseline and posture-responsive time intervals. The time interval of each of the baseline time period and posture responsive may be days, weeks, months, years, durations between two clinician sessions, or some other period of time. Each of time intervals may also be of varying time durations. Patient information graph 232 is generally described as indicating respective percentages of time in which patient 12 resides in a given posture state during a time interval. Percentages, absolute times, or other metrics may be used and obtained in variety of ways.

Screen 230 of user interface 228 may present graph 232 to a user, such as a clinician or patient, to compare the baseline proportional posture state information to posture-responsive proportional posture state information generated by programmer 20, as described above. Graph 232 may facilitate to the evaluation of the posture-responsive therapy delivered to patient 12 based on the posture state behavior of patient 12 prior to delivery of posture-responsive therapy compared to that of the posture state behavior since the posture-responsive therapy has been active. As shown on patient information graph 232 for the baseline time period, patient information graph 232 indicates that patient 12 was in was in the lying down posture 80 percent of the time, the upright posture 15 percent of the time, and the upright and active posture state only 5 percent of the time. As mentioned above, the lying down posture state may include: lying front, lying back, lying right, and lying left. The upright and active posture state indicates that patient 12 was upright in addition to being engaged in some sort of activity, such as walking or running, as opposed to remaining stationary. In contrast, patient information graph 232 shows that in the time period since posture-responsive therapy has been active, patient 12 was in the lying down posture 45 percent of the time, the upright position 30 percent of the time, and the upright and active posture 20 percent of the time. Based on graph 232, a clinician or patient may recognize a trend indicating that patient 12 is in the upright posture state for a much greater duration after PRS therapy has been active than when compared to the time period prior to PRS therapy being activated. In some cases, a clinician or patient may infer from such data that patient 12 may be responding beneficially to posture-responsive therapy.

Figure 14:
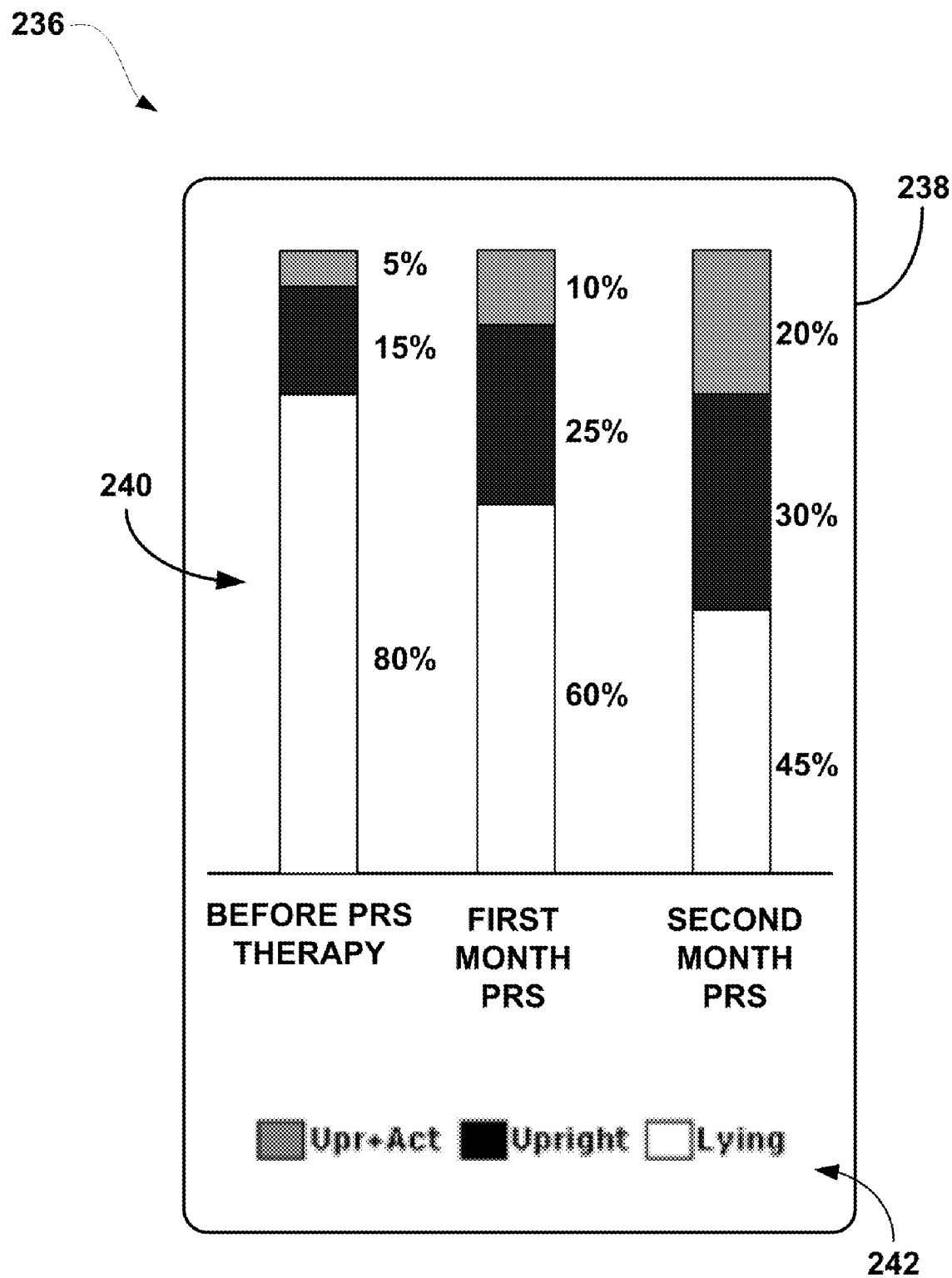
FIG. 14 is conceptual diagram illustrating an example user interface presenting a comparison of baseline proportional posture information to posture-responsive proportional posture information.

FIG. 14 is another conceptual diagram illustrating an example user interface 236 presenting a comparison of baseline proportional posture information to posture-responsive proportional posture information. Similar to FIG. 13, user interface 236 is described generally as being displayed by external programmer 20. However, user interface 236 may also be displayed by patient programmer 30, clinician programmer 60, or some other external device. In any case, user interface 236 displays baseline and posture-responsive patient information generated based on posture state data indicative of the posture state of patient 12 during time periods when posture-responsive therapy is and is not, respectively, delivered by IMD 14 to patient 12.

In the example of FIG. 14, screen 238 of user interface 236 presents patient information graph 240 and posture state key 242. Similar to patient information graph 232 (FIG. 13), patient information graph 240 displays both baseline proportional posture state information and posture-responsive posture state information consistent with that generated by processor 104 (FIG. 6) based on posture state data acquired from IMD 14 and/or external sensing device.

However, unlike graph 232 (FIG. 13), patient information graph 240 displays posture-responsive proportional posture information generated from posture state data from to distinct two time periods since PRS therapy was activated. In particular, graph 240 includes posture-responsive proportional posture state information generated from posture state data corresponding to the first month that posture-responsive therapy was delivered to patient 12 and also posture-responsive proportional posture state information generated from posture state data corresponding to the second month that posture-responsive therapy was delivered to patient 12. In this manner, screen 238 presents graph 240 to compare the baseline proportional postures state information to posture-responsive proportional posture state information generated and displayed separately according to the amount of time since the posture-responsive therapy was activated. While the posture-responsive proportional posture state information has been generated in the example of FIG. 14 according to the first month and second month of PRS therapy, other periods of time are contemplated, such as, those on the order of days, weeks, and hours. Furthermore, baseline patient information may also be generated and presented according to particular periods of time within the period of time that patient 12 was not receiving posture-responsive therapy.

Similar to graph 232 (FIG. 13), graph 240 may facilitate to the evaluation of the posture-responsive therapy delivered to patient 12 based on the posture state behavior of patient 12 prior to delivery of posture-responsive therapy compared to that of the posture state behavior since the posture-responsive therapy has been active. As shown on patient information graph 240 for the baseline time period, posture state graph 240 indicates that patient 12 was in was in the lying down posture 80 percent of the time, the upright posture 15 percent of the time, and the upright and active posture state only 5 percent of the time. As mentioned above, the lying down posture state may include: lying front, lying back, lying right, and lying left. The upright and active posture state indicates that patient 12 was upright in addition to being engaged in some sort of activity, such as walking or running, as opposed to remaining stationary. In contrast, posture duration graph 240 shows that in the first month since posture-responsive therapy has been active, patient 12 was in the lying down posture 60 percent of the time, the upright position 25 percent of the time, and the upright and active posture 10 percent of the time. Moreover, posture duration graph 240 shows that in the second month since posture-responsive therapy has been active, patient 12 was in the lying down posture 45 percent of the time, the upright position 30 percent of the time, and the upright and active posture 20 percent of the time. Based on graph 240, a clinician or patient may recognize a trend indicating that patient 12 is in the upright posture state for a much greater duration after PRS therapy has been active than when compared to the time period prior to PRS therapy being activated, and that the effect on the posture state behavior of patient 12 from PRS therapy is continuing to increase as time progresses. In some cases, a clinician or patient may infer from such data that patient 12 may be responding beneficially to posture-responsive therapy.

Figure 15:
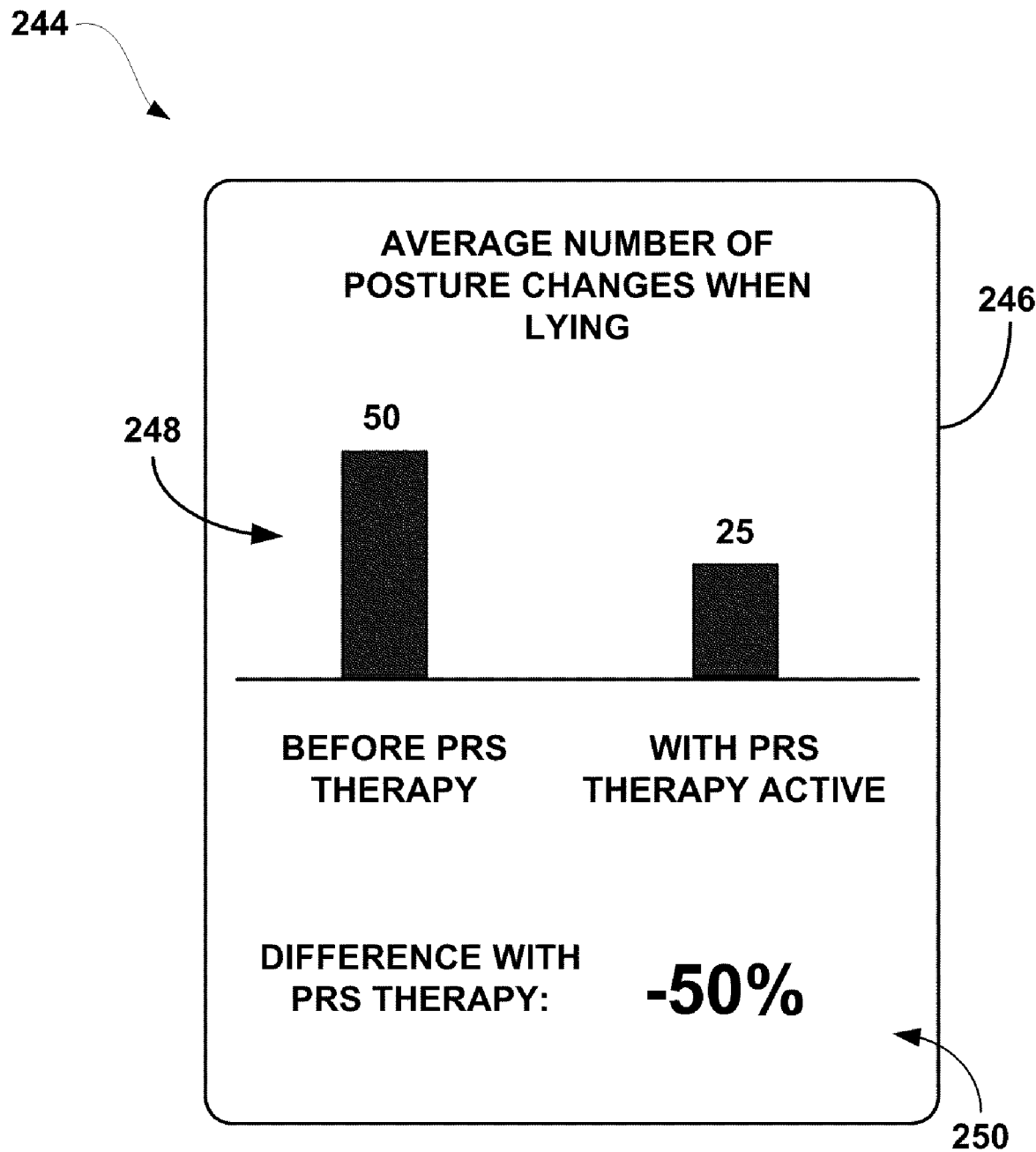
FIG. 15 is a conceptual diagram illustrating an example user interface presenting a comparison of baseline sleep quality information to posture-responsive sleep quality information.

FIG. 15 is a conceptual diagram illustrating an example user interface 244 presenting a comparison of baseline sleep quality information to posture-responsive sleep quality information. Similar to FIG. 13, user interface 244 is described generally as being displayed by external programmer 20. However, user interface 236 may also be displayed by patient programmer 30, clinician programmer 60, or some other external device. In any case, user interface 236 displays baseline and posture-responsive sleep quality information generated based on posture state data indicative of the posture state of patient 12 during time periods when posture-responsive therapy is and is not, respectively, delivered by IMD 14 to patient 12.

In the example of FIG. 15, screen 246 of user interface presents patient information graph 248 and difference indicator 250. Patient information graph 248 displays both baseline sleep quality information and posture-responsive sleep quality information consistent with that generated by processor 104 (FIG. 6) based on posture state data acquired from IMD 14 and/or external sensing device 15. Patient information graph 248 includes the average number of posture changes made by patient 12 when lying. A posture change when lying may be defined as any change in posture state between the posture states of lying front, lying back, lying right, and lying left.

Screen 246 of user interface 244 may present graph 248 to a user, such as a clinician or patient, to compare the baseline sleep quality information to posture-responsive sleep quality information generated by programmer 20, as described above. Graph 240 may facilitate to the evaluation of the posture-responsive therapy delivered to patient 12 based on the posture state behavior of patient 12 prior to delivery of posture-responsive therapy compared to that of the posture state behavior since the posture-responsive therapy has been active. Patient information graph 240 in FIG. 15 includes two bar charts with numerical text that indicates that patient 12 made an average of 50 posture state changes when lying before PRS therapy was delivered and an average of 25 posture state changes when lying with PRS therapy active. The time interval for the baseline and posture-responsive sleep quality information may be days, weeks, months, or any other appropriate time period. Furthermore, difference indicator 250 presented on screen 246 indicates the percent difference between the baseline sleep quality information and posture-responsive sleep quality information shown in patient information graph 248. In particular, the text of difference indicator 250 indicates that the average number of posture changes by patient 12 with PRS active is 50% less than the average number of posture changes before PRS was delivered, i.e., during the time period corresponding to the baseline sleep quality information. Based on graph 248, a clinician or patient may recognize that patient 12 is averaging less lying posture changes since PRS therapy has been active compared to the time period prior to PRS therapy being activated and, in particular, that the average number had decreased by 50%. In some cases, a clinician or patient may infer from such data that patient 12 may be responding beneficially to posture-responsive therapy, at least in terms of sleep quality.

Figure 16:
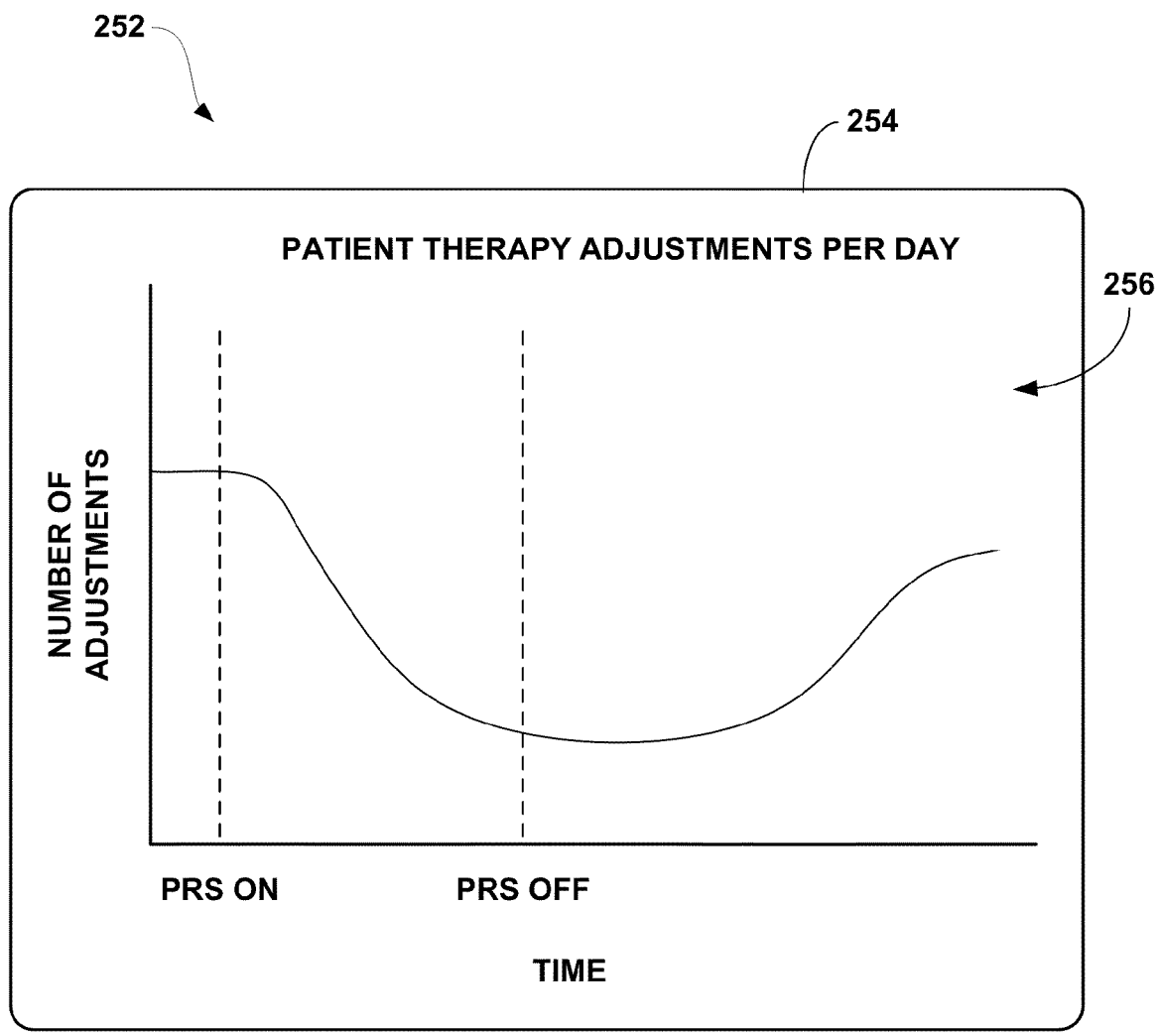
FIG. 16 is a conceptual diagram illustrating an example user interface presenting a comparison of baseline therapy adjustment information to posture-responsive therapy adjustment information.

FIG. 16 is a conceptual diagram illustrating an example user interface 252 presenting a comparison of baseline therapy adjustment information to posture-responsive therapy adjustment information. Similar to FIG. 13, user interface 252 is described generally as being displayed by external programmer 20. However, user interface 252 may also be displayed by patient programmer 30, clinician programmer 60, or some other external device. In any case, user interface 252 displays baseline and posture-responsive therapy adjustment information generated based on therapy adjustment data indicative of therapy adjustments made by patient 12 during time periods when posture-responsive therapy is and is not, respectively, delivered by IMD 14 to patient 12.

In the example of FIG. 16, screen 254 of user interface 252 presents patient information graph 256. Patient information graph 256 displays both baseline therapy adjustment information and posture-responsive therapy adjustment information consistent with that generated by processor 104 (FIG. 6). Further, patient information graph 256 displays baseline therapy adjustment information corresponding to individual time periods both before PRS therapy was turned on and after the PRS was turned off, as well as displaying posture-responsive therapy adjustment information corresponding to the time period when PRS was turned on. The posture adjustment information is presented according to the number of patient therapy adjustments per day, which may be generated by processor 105 (FIG. 6) based on the therapy adjustment data acquired from IMD 14 and/or external sensing device 15. The therapy adjustment information may generated by processor 105 for any desired time period, including minutes, hours, days, weeks, and months. In some cases, the therapy adjustment information, or any patient information, may be calculated relative to programming sessions.

Screen 254 of user interface 252 may present graph 256 to a user, such as a clinician or patient, to compare the baseline therapy adjustment information to posture-responsive therapy adjustment information generated by programmer 20, as described above. Graph 252 may facilitate to the evaluation of the posture-responsive therapy delivered to patient 12 based on the posture state behavior of patient 12 prior to delivery of posture-responsive therapy compared to that of the posture state behavior since the posture-responsive therapy has been active. Patient information graph 240 in FIG. 15 includes a plot indicating that the number of daily therapy adjustments made by patient 12 began decreasing around the time that PRS was turned on, and then leveled off at approximately the time that PRS was turned off. Graph 256 also indicates that the number of posture changes made by patient 12 per day was maintained at the approximate level observed when the PRS was turned off for a certain period of time after PRS was turned off, then increasing some time after. The time interval for the baseline and posture-responsive adjustment information shown in graph 256 may be days, weeks, months, or any other appropriate time period. Based on graph 256, a clinician or patient may recognize that the number of daily therapy changes for patient 12 decreased when PRS therapy was turned on compared to the time period prior to PRS therapy being turned on. Additionally, based on graph 256, a clinician or patient may recognize that the effects of PRS therapy with respect to the number of therapy changes per day may realized to some extent ever after PRS therapy has been turned off. In some cases, a clinician or patient may infer from such data that patient 12 may be responding beneficially to posture-responsive therapy, at least in terms of therapy adjustments.

Baseline and posture-responsive patient information may be presented to a user in any manner that allows for the user to evaluate one or more aspects of the posture state and/or therapy adjustment behavior of a patient receiving posture-responsive therapy by comparison. FIGS. 13-15 are only examples of techniques for presenting such patient information to a user. Other examples of techniques for presenting patient information to a user, whether it be baseline, posture-responsive patient information or both, may also include those examples described in co-pending U.S. patent application to Skelton et al., filed on the same date as the present application and entitled "DATA ANALYSIS FOR POSTURE RESPONSIVE THERAPY" Ser. No. 12/433,632and co-pending U.S. Provisional Patent Application Ser. No. 61/080,000, to Skelton, et al., filed Jul. 11, 2008, titled "DATA ANALYSIS FOR POSTURE RESPONSIVE THERAPY".

Certain examples have been described in which information is processed and presented to a user in one form or another, e.g., the presentation of baseline and posture-responsive patient information generated based on appropriate patient data. In some examples, information processed and presented to a user may be processed and/or presented via any suitable external programming device, such as programmer 20, patient programmer 30 (FIG. 2), and clinician programmer 60 (FIG. 3). In other examples, the information may be processed and/or presented via a computer that communicates with programmers 20, 30, and 60, and/or IMD 14.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples of the disclosure have been described. Various modifications may be made without departing from the scope of the claims. These and other examples are within the scope of the following claims.

The invention claimed is:

1. A method comprising:
acquiring first patient data, wherein the first patient data comprises at least one of first posture state data indicative of a plurality of posture states of a patient during a first time period or first therapy adjustment data indicative of a plurality of patient therapy adjustments during the first time period;
generating baseline patient information based at least in part on the first patient data; and
comparing the baseline patient information to patient information generated based on second patient data, wherein the second patient data comprises at least one of second posture state data indicative of a plurality of posture states of the patient during a second time period or second therapy adjustment data indicative of a plurality of patient therapy adjustments during the second time period,
wherein therapy is not delivered to the patient according to a detected posture state of the patient during the first time period, and therapy is delivered to the patient according to the detected posture state of the patient during the second time period, wherein the acquiring, generating, and comparing are performed via one or more processors.

2. The method of claim 1, wherein the baseline patient information comprises at least one of baseline posture state information or baseline therapy adjustment information.

3. The method of claim 2, wherein the baseline postures state information comprises at least one of baseline sleep quality information, baseline proportional posture information, or baseline posture state adjustment information.

4. The method of claim 2, wherein the baseline therapy adjustment information comprises a number of therapy adjustments received over the first time period.

5. The method of claim 1, further comprising modifying one or more aspects of the therapy based on the comparison of the baseline patient information and the patient information.

6. The method of claim 5, wherein modifying one or more aspects of the therapy based on the comparison comprises at least one of terminating, adjusting, or initiating one or more aspects of posture-responsive therapy.

7. The method of claim 1, further comprising generating the first posture state data, wherein generating the first posture state data comprises receiving posture state sensor data and detecting the posture state of the patient based on the posture state sensor data.

8. The method of claim 1, wherein comparing the baseline patient information to patient information generated based on the second patient data comprises presenting at least a portion of the baseline patient information and at least a portion of the patient information to a user via a user interface display of an external device.

9. The method of claim 1, wherein comparing the baseline patient information to patient information generated based on the second patient data comprises determining one or more differences between the baseline patient information and the patient information generated based on the second patient data.

10. The method of claim 9, further comprising presenting the one or more differences between the baseline patient information and the patient information generated based on the second patient data to a user via a user interface display of an external device.

11. The method of claim 1, further comprising:
acquiring the second patient data; and
generating the patient information based at least in part on the second patient data.

12. The method of claim 1, wherein at least a portion of the first time period is after the second time period.

13. The method of claim 1, wherein the first time period comprises a time period after the second time period and a time period before the second time period, wherein the baseline patient information comprises first baseline patient information based on patient data from the time period after the second time period and second baseline patient information based on patient data from the time period before the second time period.

14. A system comprising:
a processor configured to acquire first patient data, generate baseline patient information based at least in part on the first patient data, and compare the baseline patient information to patient information generated based on second patient data,
wherein the first patient data comprises at least one of first posture state data indicative of a plurality of posture states of a patient during a first time period or first therapy adjustment data indicative of a plurality of patient therapy adjustments during the first time period,
wherein the second patient data comprises at least one of second posture state data indicative of a plurality of posture states of the patient during a second time period or second therapy adjustment data indicative of a plurality of patient therapy adjustments during the second time period,
wherein therapy is not delivered to the patient according to a detected posture state of the patient during the first time period, and therapy is delivered to the patient according to the detected posture state of the patient during the second time period.

15. The system of claim 14, wherein the baseline patient information comprises at least one of baseline posture state information or baseline therapy adjustment information.

16. The system of claim 15, wherein the baseline postures state information comprises at least one of sleep quality baseline information, proportional posture baseline information, or posture state adjustment information.

17. The system of claim 15, wherein the baseline therapy adjustment information comprises a number of therapy adjustments received over the first time period.

18. The system of claim 14, wherein the processor is configured to modify one or more aspects of the therapy based on the comparison of the baseline patient information and the patient information.

19. The system of claim 18, wherein the processor is configured to modify the one or more aspects of the therapy by at least one of terminating, adjusting, or initiating one or more aspects of posture-responsive therapy.

20. The system of claim 14, wherein the processor is configured to generate the first posture state data, wherein the processor generates the first posture state data by at least receiving posture state sensor data and detecting the posture state of the patient based on the posture state sensor data.

21. The system of claim 14, further comprising an external device comprising a user interface display, wherein the processor compares the baseline patient information to patient information generated based on second patient data by at least presenting at least a portion of the baseline patient information and at least a portion of the patient information to a user via the user interface display.

22. The system of claim 14, wherein the processor compares the baseline patient information to patient information generated based on second patient data by at least determining one or more differences between the baseline patient information and the patient information generated based on the second patient data.

23. The system of claim 22, further comprising an external device comprising a user interface display, wherein the processor presents the one or more differences between the baseline patient information and the patient information to a user via the user interface display.

24. The system of claim 14, wherein the processor is configured to acquire the second patient data during the second time period, and generate the patient information based at least in part on the second patient data.

25. The system of claim 14, wherein at least a portion of the first time period is after the second time period.

26. The system of claim 14, wherein the first time period comprises a time period after the second time period and a time period before the second time period, wherein the baseline patient information comprises first baseline patient information based on the patient data from the time period after the second time period and second patient information based on patient data from the time period before the second time period.

27. The system of claim 14, further comprising an external programmer comprising the processor.

28. The system of claim 14, wherein the processor comprises a first processor and a second processor, wherein the first processor acquires the first patient data and generates the baseline patient information, and the second processor compares the baseline patient information to the patient information generated based on second patient data.

29. The system of claim 28, further comprising a medical device including the first processor, and a programmer including the second processor.

30. A system comprising:
means for acquiring first patient data, wherein the first patient data comprises at least one of first posture state data indicative of a plurality of posture states of a patient during a first time period or first therapy adjustment data indicative of a plurality of patient therapy adjustments during the first time period;
means for generating baseline patient information based at least in part on the first patient data; and
means for comparing the baseline patient information to patient information generated based on second patient data, wherein the second patient data comprises at least one of second posture state data indicative of a plurality of posture states of the patient during a second time period or second therapy adjustment data indicative of a plurality of patient therapy adjustments during the second time period,
wherein therapy is not delivered to the patient according to a detected posture state of the patient during the first time period, and therapy is delivered to the patient according to the detected posture state of the patient during the second time period.

31. A computer-readable storage medium comprising instruction to cause one or more processor to:
acquire first patient data, wherein the first patient data comprises at least one of first posture state data indicative of a plurality of posture states of a patient during a first time period or first therapy adjustment data indicative of a plurality of patient therapy adjustments during the first time period;

generate baseline patient information based at least in part on the first patient data; and compare the baseline patient information to patient information generated based on second patient data, wherein the second patient data comprises at least one of second posture state data indicative of a plurality of posture states of the patient during a second time period or second therapy adjustment data indicative of a plurality of patient therapy adjustments during the second time period, wherein therapy is not delivered to the patient according to a detected posture state of the patient during the first time period, and therapy is delivered to the patient according to the detected posture state of the patient during the second time period.

* * * * *